US012708464B2

(12) United States Patent
Yu et al.

(10) Patent No.: US 12,708,464 B2
(45) Date of Patent: Aug. 18, 2026

(54) METHODS, SYSTEMS, DEVICE, AND STORAGE MEDIUMS FOR OBSTACLE AVOIDANCE OF SURGICAL ROBOTS

(71) Applicant: WUHAN UNITED IMAGING SURGICAL CO., LTD., Wuhan (CN)

(72) Inventors: Supu Yu, Wuhan (CN); Tong Wu, Wuhan (CN); Yang Zhang, Wuhan (CN); Quanquan Wang, Wuhan (CN); Qiang Xie, Shanghai (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 93 days.

(21) Appl. No.: 18/651,614

(22) Filed: Apr. 30, 2024

(65) Prior Publication Data

US 2024/0285356 A1 Aug. 29, 2024

Related U.S. Application Data

(63) Continuation of application No. PCT/CN2022/129027, filed on Nov. 1, 2022.

(30) Foreign Application Priority Data

Nov. 2, 2021 (CN) ......................... 202111287771.X

(51) Int. Cl.
*A61B 34/30* (2016.01)
*A61B 17/00* (2006.01)
(Continued)

(52) U.S. Cl.
CPC .............. *A61B 34/30* (2016.02); *A61B 17/00* (2013.01); *A61B 34/10* (2016.02); *A61B 90/37* (2016.02);
(Continued)

(58) Field of Classification Search
CPC ......... A61B 34/30; A61B 34/10; A61B 90/37; A61B 17/00; A61B 2034/105; A61B 2034/305; A61B 2017/00725
See application file for complete search history.

(56) References Cited

U.S. PATENT DOCUMENTS

2018/0049825 A1* 2/2018 Kwon .................... A61B 90/14
2019/0163039 A1* 5/2019 Zhang .................. H04N 23/698
(Continued)

FOREIGN PATENT DOCUMENTS

CN 104933392 A 9/2015
CN 105455901 A 4/2016
(Continued)

OTHER PUBLICATIONS

The Extended European Search Report in European Application No. 22889273.3 mailed on Jan. 22, 2025, 9 pages.
(Continued)

*Primary Examiner* — Thomas E Worden
(74) *Attorney, Agent, or Firm* — Poseidon Advanced IP LLC

(57) ABSTRACT

Embodiment of the present disclosure provides a method for obstacle avoidance of a surgical robot. The method may include: collecting first data through a first acquisition device, wherein the first data is image data of a space in which a target subject is located; constructing a safety zone for the target subject based on the first data; collecting second data outside the safety zone through a second acquisition device, wherein the second data is image data of the target subject; and constructing a three-dimensional model of the target subject based on the second data, wherein the three-dimensional model of the target subject may be used for obstacle avoidance detection during an operation of the surgical robot.

20 Claims, 10 Drawing Sheets

(51) Int. Cl.
*A61B 34/10* (2016.01)
*A61B 90/00* (2016.01)

(52) U.S. Cl.
CPC ............... *A61B 2017/00725* (2013.01); *A61B 2034/105* (2016.02); *A61B 2034/305* (2016.02)

(56) References Cited

U.S. PATENT DOCUMENTS

| | | | | |
|---|---|---|---|---|
| 2020/0121267 | A1 | 4/2020 | Deutschmann | |
| 2021/0069906 | A1 | 3/2021 | Vu et al. | |
| 2021/0069907 | A1 | 3/2021 | Vu et al. | |
| 2021/0093393 | A1 | 4/2021 | Quist et al. | |
| 2021/0093407 | A1 | 4/2021 | Fredrickson et al. | |
| 2023/0016940 | A1* | 1/2023 | Lang .................... | A61B 17/142 |
| 2024/0156543 | A1 | 5/2024 | Roessler | |

FOREIGN PATENT DOCUMENTS

| | | | |
|---|---|---|---|
| CN | 109584362 | A | 4/2019 |
| CN | 110977989 | A | 4/2020 |
| CN | 112754658 | A | 5/2021 |
| CN | 112802185 | A | 5/2021 |
| CN | 113081274 | A | 7/2021 |
| CN | 113100944 | A | 7/2021 |
| CN | 114022612 | A | 2/2022 |
| WO | 2018081136 | A2 | 5/2018 |
| WO | 2020190832 | A1 | 9/2020 |
| WO | 2021059100 | A1 | 4/2021 |

OTHER PUBLICATIONS

International Search Report in PCT/CN2022/129027 mailed on Jan. 19, 2023, 8 pages.

Written Opinion in PCT/CN2022/129027 mailed on Jan. 19, 2023, 8 pages.

First Office Action in Chinese Application No. 202111287771.X mailed on Apr. 19, 2025, 17 pages.

* cited by examiner

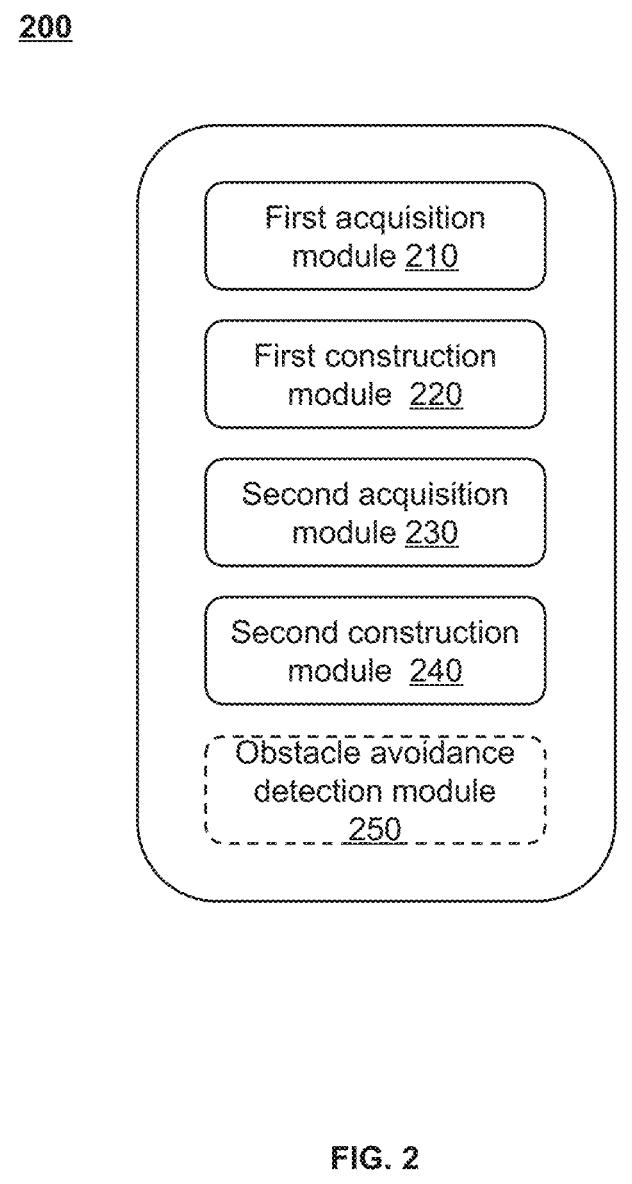

200

First acquisition module 210

First construction module 220

Second acquisition module 230

Second construction module 240

Obstacle avoidance detection module 250

FIG. 2

METHODS, SYSTEMS, DEVICE, AND STORAGE MEDIUMS FOR OBSTACLE AVOIDANCE OF SURGICAL ROBOTS

CROSS-REFERENCE TO RELATED APPLICATIONS

This application is a continuation of International Application No. PCT/CN2022/129027, filed on Nov. 1, 2022, which claims priority to Chinese Patent Application No. 202111287771.X, filed on Nov. 2, 2021, entitled "Methods, Devices, Computer Devices, and Storage Mediums for Model Construction," the entire contents of each of which are incorporated herein by reference.

TECHNICAL FIELD

The present disclosure relates to the field of robotics, and in particular, to methods, systems, devices, and storage mediums for obstacle avoidance of surgical robots.

BACKGROUND

During a neurosurgery procedure, a surgical robot moves autonomously. It is essential that the autonomous motion of the surgical robot is conducted without risk, i.e., the surgical robot must not collide with a surrounding object during the autonomous motion. The surrounding object may include the head of a patient on a surgical bed, a device worn on the head of the patient, the surgical bed, a moving doctor during the surgery, etc.

Therefore, it is desirable to provide a method, system, device, and storage medium for obstacle avoidance of a surgical robot, which are used to construct a three-dimensional model of a target subject and a three-dimensional model of a space in which the target subject is located, thereby allowing the surgical robot to actively avoid the surrounding object during the autonomous motion of the surgical robot, and improving obstacle avoidance precision.

SUMMARY

One embodiment of the present disclosure provides a method for obstacle avoidance of a surgical robot. The method may include: collecting first data through a first acquisition device, wherein the first data is image data of a space in which a target subject is located; constructing a safety zone for the target subject based on the first data; collecting second data outside the safety zone through a second acquisition device, wherein the second data is image data of the target subject; and constructing a three-dimensional model of the target subject based on the second data, wherein the three-dimensional model of the target subject is used for obstacle avoidance detection during an operation of the surgical robot.

In some embodiments, the constructing a safety zone for the target subject based on the first data may include: identifying first subset data of the target subject based on the first data, and constructing the safety zone based on the first subset data.

In some embodiments, the collecting second data outside the safety zone through a second acquisition device may include: determining a plurality of first acquisition points based on the safety zone, and sequentially collecting the second data at the plurality of first acquisition points using the second acquisition device.

In some embodiments, the determining a plurality of first acquisition points based on the safety zone may include: dividing the safety zone into a plurality of regions, and generating the plurality of first acquisition points around a periphery of the plurality of regions based on a preset generation algorithm.

In some embodiments, the sequentially collecting the second data at the plurality of first acquisition points using the second acquisition device may include: for any first acquisition point of the plurality of first acquisition points, determining whether a coverage rate of second data collected at the first acquisition point and previous first acquisition points relative to the target subject satisfies a requirement; in response to determining that the coverage rate does not satisfy the requirement, collecting second data at a next first acquisition point using the second acquisition device; and in response to determining that the coverage rate satisfies the requirement, ending the collection.

In some embodiments, the method may further include: determining whether the collected second data includes image data of a preset location of the target subject; in response to determining that the collected second data does not include the image data of the preset location of the target subject, determining a second acquisition point, and collecting the image data of the preset location of the target subject at the second acquisition point using the second acquisition device.

In some embodiments, the second acquisition device may be located at an end of a mechanical arm of the surgical robot.

In some embodiments, the target subject may include at least one of the head of a patient on a surgical bed or a device worn on the head of the patient.

In some embodiments, the method may further include: constructing an initial three-dimensional model of the space in which the target subject is located based on the first data, obtaining a three-dimensional model of the space in which the target subject is located based on the three-dimensional model of the target subject and the initial three-dimensional model of the space, and performing the obstacle avoidance detection based on the three-dimensional model of the space.

In some embodiments, the performing the obstacle avoidance detection based on the three-dimensional model of the space may include: dividing the three-dimensional model of the space into a plurality of regions, determining a simulation completeness degree for each region of the plurality of regions, and transmitting the simulation completeness degree to the surgical robot for path planning.

In some embodiments, the constructing an initial three-dimensional model of the space in which the target subject is located based on the first data may include: determining a relative position of the target subject and the first acquisition device based on the first data, adjusting a shooting angle of the first acquisition device based on the relative position, obtaining new image data captured by the first acquisition device at the adjusted shooting angle, and designating the new image data as the first data for constructing the initial three-dimensional model.

One embodiment of the present disclosure provides a system for obstacle avoidance of a surgical robot. The system may include a first acquisition module, a first construction module, a second acquisition module, and a second construction module. The first acquisition module may be configured to collect first data through a first acquisition device, wherein the first data is image data of a space in which a target subject is located. The first construction module may be configured to construct a safety zone for the target subject based on the first data. The second acquisition module may be configured to collect second data outside the safety zone through a second acquisition device, wherein the second data is image data of the target subject. The second construction module may be configured to construct a three-dimensional model of the target subject based on the second data, wherein the three-dimensional model of the target subject may be used for obstacle avoidance detection during an operation of the surgical robot.

One embodiment of the present disclosure provides a system for obstacle avoidance of a surgical robot. The system may include a first acquisition device, a second acquisition device, the surgical robot, and a processor. The first acquisition device may be configured to collect first data, wherein the first data is image data of a space in which a target subject is located. The second acquisition device may be configured to collect second data outside a safety zone of the target subject, wherein the second data is image data of the target subject. The surgical robot may be configured to perform a surgical procedure. The processor may be configured to: construct the safety zone based on the first data, and construct a three-dimensional model of the target subject based on the second data, wherein the three-dimensional model of the target subject may be used for obstacle avoidance detection during an operation of the surgical robot.

One embodiment of the present disclosure provides a device for obstacle avoidance of a surgical robot, which may include a processor and a storage, wherein the storage may be configured to store an instruction set, and the processor may be configured to execute the instruction set to implement the method for obstacle avoidance of the surgical robot.

One embodiment of the present disclosure provides a computer-readable storage medium storing computer instructions. When reading the computer instructions from the storage medium, a computer implements the method for obstacle avoidance of the surgical robot.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 is a block diagram illustrating an exemplary processor for obstacle avoidance of a surgical robot according to some embodiments of the present disclosure;

DETAILED DESCRIPTION

Figure 1:
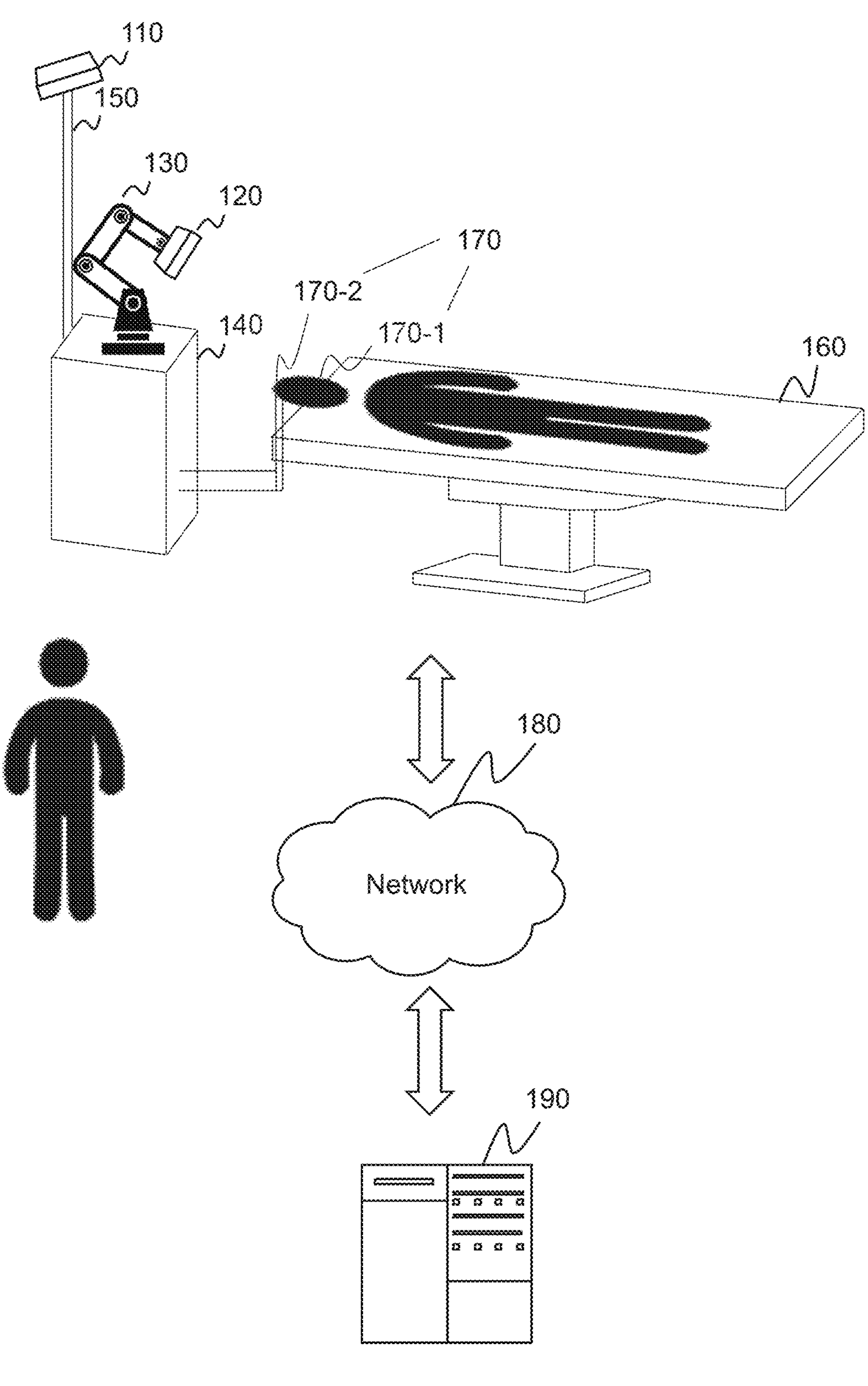
FIG. 1 is a schematic diagram illustrating an exemplary application scenario of an obstacle avoidance system of a surgical robot according to some embodiments of the present disclosure.

In order to more clearly illustrate the technical solutions of the embodiments of the present disclosure, the accompanying drawings to be used in the description of the embodiments will be briefly described below. Obviously, the accompanying drawings in the following description are only some examples or embodiments of the present disclosure, and that the present disclosure may be applied to other similar scenarios in accordance with these drawings without creative labor for those of ordinary skill in the art. Unless obviously acquired from the context or the context illustrates otherwise, the same numeral in the drawings refers to the same structure or operation.

It should be understood that "system," "device," "unit," and/or "module" as used herein is a way to distinguish between different components, elements, parts, sections, or assemblies at different levels. However, these words may be replaced by other expressions if they accomplish the same purpose.

As indicated in the present disclosure and in the claims, the singular forms "a," "an," and "the" may be intended to include the plural forms as well, unless the context clearly indicates otherwise. In general, the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

Flowcharts are used in the present disclosure to illustrate the operations performed by the system according to some embodiments of the present disclosure. It should be understood that the operations described herein are not necessarily executed in a specific order. Instead, they may be executed in reverse order or simultaneously. Additionally, one or more other operations may be added to these processes, or one or more operations may be removed from these processes.

FIG. 1 is a schematic diagram illustrating an exemplary application scenario of an obstacle avoidance system 100 of a surgical robot according to some embodiments of the present disclosure. In some embodiments, the obstacle avoidance system 100 may include a first acquisition device 110, a second acquisition device 120, a surgical robot 130, a surgical cart 140, a support frame 150, a surgical bed 160, a target subject 170, a network 180, and a processor 190. In some embodiments, the obstacle avoidance system 100 may further include a storage device and/or a user terminal (not shown in drawings).

In some embodiments, the surgical robot 130 may be disposed on the surgical cart 140, the first acquisition device 110 may be disposed on the support frame 150 of the surgical cart 140, and the second acquisition device 120 may be located at an end of a mechanical arm of the surgical robot 130.

The first acquisition device 110 refers to a device configured to acquire image data of a space where the target subject is located. For example, the first acquisition device 110 may include a structured light depth camera, a time-of-flight depth camera, a binocular stereo camera, etc. As another example, the first acquisition device 110 may also be other image capture devices apart from the structured light depth camera, the time-of-flight depth camera, the binocular stereo camera. The image data may include depth image data (e.g., three-dimensional image data), RGB (e.g., RGB color mode) image data, etc. In some embodiments, the space where the target subject is located includes a region where the surgical bed in the operating room is located. In some embodiments, the first acquisition device 110 may be installed on the support frame 150 of the surgical cart 140 for acquiring first data. In some embodiments, a pose (e.g., a position, a shooting angle, a height, etc.) of the first acquisition device 110 may be adjusted through the surgical cart 140 and the support frame 150 according to the needs of different surgical scenarios. After being adjusted, the pose of the first acquisition device 110 does not change during the same surgical procedure. In some embodiments, the first acquisition device 110 may also be installed in other ways, for example, the first acquisition device 110 may be installed on an electric lifting hanger of the camera, which is not limited herein. More descriptions regarding the target subject and the first data may be found in FIG. 3 and the related descriptions thereof.

The second acquisition device 120 refers to a device configured to acquire image data of the target subject. For example, the second acquisition device 120 may include a structured light depth camera, a time-of-flight depth camera, a binocular stereo camera, etc. The second acquisition device 120 may also be other image capture devices, which is not limited herein. The image data may include depth image data (e.g., three-dimensional image data), RGB image data, etc. In some embodiments, the second acquisition device 120 may be installed at an end of the mechanical arm of the surgical robot 130 for acquiring second data. In some embodiments, the second acquisition device 120 may also be installed at other positions such as a middle section of the mechanical arm of the surgical robot 130. The closer the position is to the end of the mechanical arm of the surgical robot 130, the higher a degree of freedom of the second acquisition device 120, and the installation position of the second acquisition device on the mechanical arm of the surgical robot 130 may be selected by those skilled in the art according to requirements for freedom. In some embodiments, the first acquisition device 110 and the second acquisition device 120 may not be the same acquisition device, and the first acquisition device 110 and the second acquisition device 120 may be respectively disposed at the above-mentioned positions. In some embodiments, the first acquisition device 110 and the second acquisition device 120 may be integrated into a same acquisition device. For example, one of the first acquisition device 110 and the second acquisition device 120 is canceled, and functions of the first acquisition device 110 and the second acquisition device 120 are implemented by the other of the first acquisition device 110 and the second acquisition device 120. The integrated acquisition device may be installed at the end of the mechanical arm of the surgical robot 130, or at other locations on the mechanical arm such as the middle end of the mechanical arm. During use, the medical staff may first drag the mechanical arm to move the above-mentioned integrated acquisition device directly above the patient's face to collect the first data, and a safe zone may be constructed for the target subject based on the first data, and then the mechanical arm may move autonomously around the target subject outside the safe zone to collect the second data to build the three-dimensional model of the target subject. More descriptions regarding the second data may be found in FIG. 3 and the related descriptions thereof.

The surgical robot 130 refers to an instrument that provides support for doctors to perform surgical operations. For example, the surgical robot 130 may include an operating surgical robot, a positioning surgical robot, etc. In some embodiments, the mechanical arm of the surgical robot 130 may drive the second acquisition device 120 to move in the space where the target subject is located, allowing the second acquisition device 120 to collect second data sequentially at multiple first acquisition points to ensure comprehensive and accurate data collection.

The surgical cart 140 refers to a cart for carrying and transferring medical equipment. In some embodiments, the surgical cart 140 may be provided with the support frame 150 for supporting the first acquisition device 110. In some embodiments, the surgical robot 130 may be installed on the surgical cart 140. The surgical bed 160 may be used to support the patient during surgery. For example, the surgical bed 160 may be a general surgical bed, a specialized surgical bed, etc.

The target subject 170 refers to the head of the patient on the surgical bed or a device worn on the head of the patient. For example, the target subject 170 may include the head 170-1 of the patient and the device 170-2 worn on the head 170-1. The device worn on the head refers to a device used to fix the head. For example, the device worn on the head may include a C-shaped head frame, a square head frame, etc.

The network 180 may connect various components of the obstacle avoidance system 100 and/or connect the obstacle avoidance system 100 with an external resource. The network 180 enables communication between the various components of the obstacle avoidance system 100 and between the obstacle avoidance system 100 and external components, thereby facilitating the exchanges of data and/or information. For example, the first data collected by the first acquisition device 110 and the second data collected by the second acquisition device 120 may be transmitted to the processor 190 for processing via the network 180. As another example, the processor 190 may send a safety zone to the surgical robot 130 for the second acquisition device to avoid collision with the target subject 170 when collecting second data outside the safety zone. As still another example, the processor 190 may transmit a three-dimensional model of the space where the target subject is located to the surgical robot 130 via the network 180 for obstacle avoidance detection.

In some embodiments, the network 180 may be any one of a wired network and a wireless network, or a combination thereof. For example, the network 180 may include a cable network, a fiber optic network, a telecommunications network, the Internet, a local area network (LAN), a wide area network (WAN), a wireless LAN (WLAN), a metropolitan area network (MAN), a public switched telephone network (PSTN), a Bluetooth network, a ZigBee network, a near field communication (NFC) network, a device internal bus, a device internal line, a cable connection, or any combination thereof. The network that connects the various components of the obstacle avoidance system 100 may be one or more of the aforementioned networks.

The processor 190 may process data and/or information obtained from other devices or system components. Based on the data, information, and/or processing results, the processor 190 may execute program instructions to perform one or more functions described in the present disclosure. For example, the processor 190 may obtain the first data and the second data and process them to obtain a three-dimensional model of the target subject 170 for obstacle avoidance detection during operation of the surgical robot.

In some embodiments, the processor 190 may include one or more sub-processing devices (e.g., single-core processing devices or multi-core/multi-chip processing devices). Merely by way of example, the processor 190 may include a central processing unit (CPU), an application-specific integrated circuit (ASIC), an application-specific instruction processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction set computer (RISC), a microprocessor, or any combination thereof.

In the application scenario of the obstacle avoidance system 100 of a surgical robot, prior to a surgery, medical personnel may push the surgical cart 140 equipped with the surgical robot 130 and the support frame 150 to a surgical station, fix the head of the patient 170-1 and the device 170-2 worn on the head, and then install the second acquisition device 120 at an end of the mechanical arm of the surgical robot 130. The medical personnel click a start button on an interactive interface, and the obstacle avoidance system would automatically perform a sensing part workflow, which may include:

The processor 190 may collect the first data via the first acquisition device 110 and construct the safety zone for the target subject 170 based on the first data. Then, the processor 190 may control the second acquisition device 120 at an end of the mechanical arm of the surgical robot 130 to collect the second data outside the safety zone. The processor 190 may determine whether the collected second data includes image data of a preset location of the target subject. If the collected second data does not include the image data of the preset location of the target subject, the processor 190 may determine a second acquisition point and collect image data of the preset location of the target subject at the second acquisition point using the second acquisition device 120, and designate the collected image data at the second acquisition point as the second data. The preset location of the target subject includes the face of the patient.

Facial registration may be performed based on the second data including the face of the patient, and after outputting and displaying the registration result, precise obstacle avoidance during autonomous motion of the mechanical arm may be achieved based on the registration result.

The mechanical arm of the surgical robot 130 may return to its initial pose, and after the medical personnel disassembles the second acquisition device 120, the subsequent workflow is executed. For example, after a medical instrument (e.g., a bone drill, etc.) is installed at an end of the mechanical arm, the surgical robot 130 may perform, based on the registration result and the three-dimensional model of the space where the target subject is located, the autonomous motion and obstacle avoidance during the autonomous motion. During the surgery, the first acquisition device 110 may capture the space where the target subject is located in real-time and obtain the status of the medical personnel. During motion, the mechanical arm of the surgical robot 130 actively avoids the medical personnel to ensure the safety of the surgery.

Since the medical personnel only need to install the second acquisition device 120, click the start button, and retract the second acquisition device 120 during the sensing part workflow, a highly automated workflow can be achieved, greatly improving the efficiency of the medical personnel.

FIG. 2 is a block diagram illustrating an exemplary processor 200 for obstacle avoidance of a surgical robot according to some embodiments of the present disclosure. The processor 200 may be a specific implementation of the processor 190 shown in FIG. 1.

In some embodiments, the processor 200 may include a first acquisition module 210, a first construction module 220, a second acquisition module 230, and a second construction module 240. In some embodiments, the processor 200 may also include an obstacle avoidance detection module 250.

The first acquisition module 210 may be configured to collect first data through the first acquisition device, wherein the first data includes image data of a space where a target subject is located.

In some embodiments, the second acquisition device may be located at an end of a mechanical arm of the surgical robot.

In some embodiments, the target subject may be at least one of the head of a patient on a surgical bed or a device worn on the head of the patient.

The first construction module 220 may be configured to construct a safety zone for the target subject based on the first data.

In some embodiments, the first construction module 220 may be further configured to identify first subset data of the target subject based on the first data and construct the safety zone based on the first subset data.

The second acquisition module 230 may be configured to collect second data outside the safety zone through the second acquisition device, wherein the second data includes image data of the target subject.

In some embodiments, the second acquisition module 230 may be further configured to determine a plurality of first acquisition points based on the safety zone and sequentially collect the second data at the plurality of first acquisition points using the second acquisition device.

In some embodiments, the second acquisition module 230 may be further configured to, for any first acquisition point of the plurality of first acquisition points, determine whether a coverage rate of second data collected at the first acquisition point and previous first acquisition points relative to the target subject satisfies a requirement. In response to determining that the coverage rate does not satisfy the requirement, the second acquisition module 230 may collect second data at a next first acquisition point using the second acquisition device. In response to determining that the coverage rate satisfies the requirement, the second acquisition module 230 may end the collection.

In some embodiments, the second acquisition module 230 may be further configured to determine whether the collected second data includes image data of a preset location of the target subject. In response to determining that the collected second data does not include the image data of the preset location of the target subject, the second acquisition module 230 may determine a second acquisition point and collect the image data of the preset location of the target subject at the second acquisition point using the second acquisition device, and designate the collected image data as the second data.

The second construction module 240 may be configured to construct a three-dimensional model of the target subject based on the second data, wherein the three-dimensional model of the target subject may be used for obstacle avoidance detection during the operation of the surgical robot.

The obstacle avoidance detection module 250 may be configured to construct an initial three-dimensional model of the space in which the target subject is located based on the first data, obtain a three-dimensional model of the space in which the target subject is located based on the three-dimensional model of the target subject and the initial three-dimensional model of the space, and perform the obstacle avoidance detection based on the three-dimensional model of the space.

In some embodiments, the obstacle avoidance detection module 250 may be further configured to determine a relative position of the target subject and the first acquisition device based on the first data, adjust a shooting angle of the first acquisition device based on the relative position, obtain new image data captured by the first acquisition device at the adjusted shooting angle, and designate the new image data as the first data for constructing the initial three-dimensional model.

More descriptions regarding the first acquisition module 210, the first construction module 220, the second acquisition module 230, the second construction module 240, and the obstacle avoidance detection module 250 may be found in FIGS. 3-9 and their corresponding descriptions.

It should be understood that the processor 200 and its modules shown in FIG. 2 may be implemented in various ways. It should be noted that the descriptions of the processor 200 and its modules provided above are for descriptive convenience only and do not limit the present disclosure to the embodiments mentioned. It should be understood that for those skilled in the art, after understanding the principle of the present disclosure, various modules may be combined arbitrarily or constitute subsystems connected with other modules without departing from this principle. In some embodiments, the first acquisition module, the first construction module, the second acquisition module, the second construction module, and the obstacle avoidance detection module disclosed in FIG. 2 may be different modules in a system, or one module that can implement the functions of two or more of the above modules. For example, various modules may share a storage module, or each module may have its own storage module. Such variations are within the scope of the present disclosure.

Figure 3:
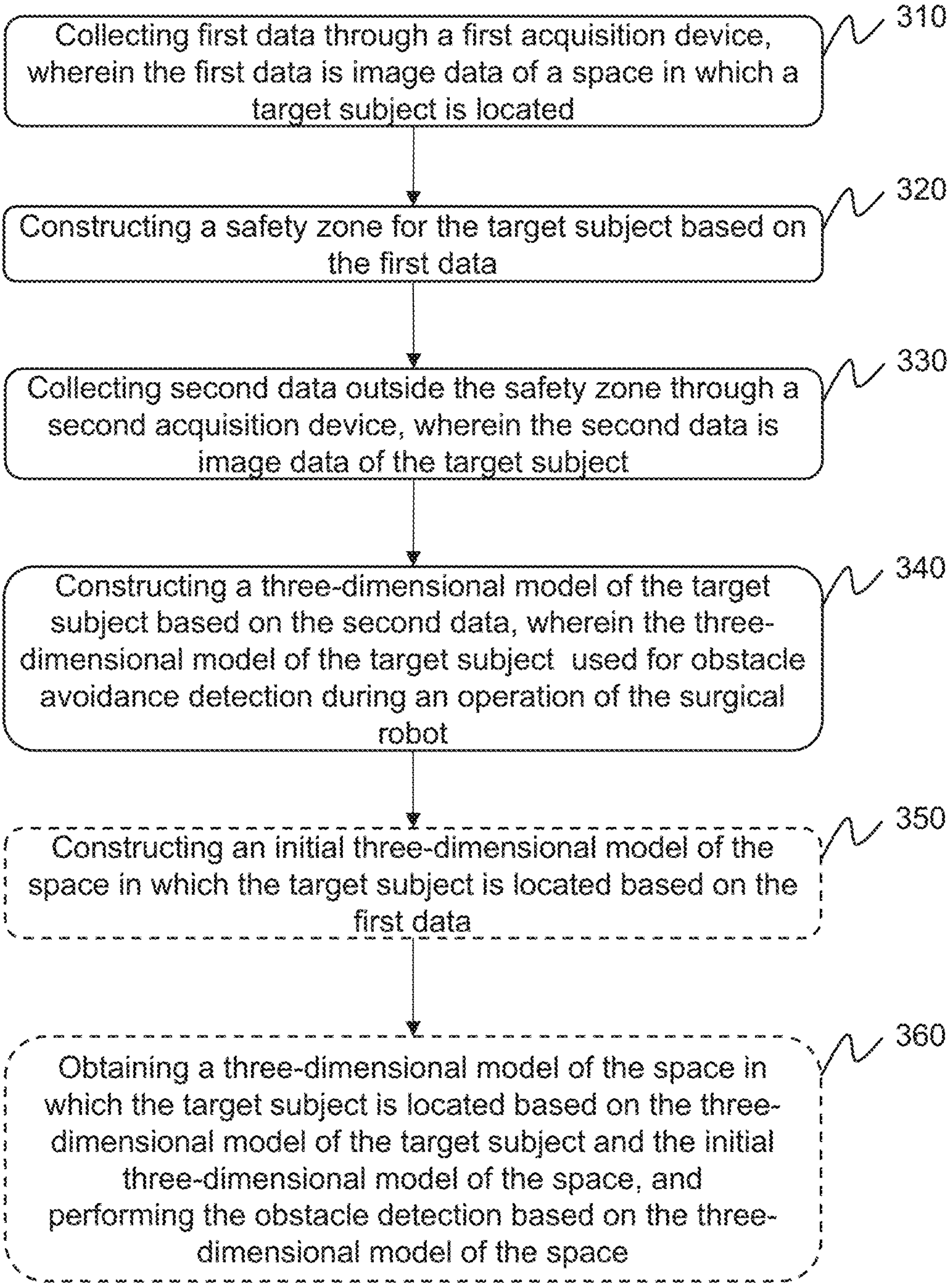
FIG. 3 is a flowchart illustrating an exemplary process for obstacle avoidance of a surgical robot according to some embodiments of the present disclosure.

FIG. 3 is a flowchart illustrating an exemplary process for obstacle avoidance of a surgical robot according to some embodiments of the present disclosure. As shown in FIG. 3, process 300 includes the following operations. In some embodiments, one or more operations of process 300 shown in FIG. 3 may be implemented in the obstacle avoidance system 100 shown in FIG. 1. For example, process 300 shown in FIG. 3 may be stored in a storage device in the form of instructions that can be called and/or executed by the processor 190.

In 310, first data may be collected through a first acquisition device, wherein the first data may include image data of a space in which a target subject is located. In some embodiments, operation 310 may be executed by the first acquisition module 210.

The first acquisition device refers to a device for collecting the first data. For example, the first acquisition device may be a structured light depth camera, a time-of-flight depth camera, a binocular stereo camera, or the like. In some embodiments, the first acquisition device may be the binocular stereo camera, and the camera of the binocular stereo camera is a binocular camera. The binocular camera may include a projector and two detectors. The projector may project a certain pattern of structured light (e.g., infrared light) onto a surface of an object in the space where the target subject is located. The structured light reflected from the surface of the object in the space where the target subject is located is received by the detectors, thereby obtaining the first data modulated by a shape of the surface of the object in the space where the target subject is located. The structured light emitted by the projector may include stripe-patterned structured light, dot-patterned structured light, chessboard-patterned structured light, or any other form of structured light. In some embodiments, the camera in the first acquisition device may include only a projector and one detector. In some embodiments, the camera in the first acquisition device may include a projector and two detectors. In some embodiments, the first acquisition device may include other types of depth cameras, which is not limited herein.

In some embodiments, an auxiliary lighting device may be provided on the first acquisition device. When the processor 190 detects that an environment light intensity is lower than a preset light intensity threshold, the resolution of an image formed by the first data collected by the first acquisition device is lower than a preset resolution threshold, and/or the noise of the image formed by the first data collected by the first acquisition device is higher than a preset noise threshold, the auxiliary lighting device may be controlled to provide auxiliary lighting to the space where the target subject is located. The preset light intensity threshold, the preset resolution threshold, and the preset noise threshold may be set based on experience. The environment light intensity may be determined based on a light intensity meter, or the like; the image resolution may be determined based on an algorithm such as Neural Image Assessment (NIMA), or the like; the image noise may be determined based on an algorithm such as a uniform area technique, a block technique, a noise estimation technique, or the like. In some embodiments, the auxiliary lighting device may be disposed on other positions (e.g., on a support frame) apart from the first acquisition device.

The first data refers to data that reflect the conditions of various objects in the space where the target subject is located, such as the positions and shape characteristics of the various objects in the space where the target subject is located. In some embodiments, the first data may include a dataset (e.g., three-dimensional spatial information of points on the surface of various objects in the space where the target subject is located) of various objects in the space where the target subject is located. In some embodiments, the first data may include depth image data, RGB image data, three-dimensional point cloud data, or the like. In some embodiments, the first data may include image data of a patient, a medical personnel, a medical diagnostic auxiliary device, or the like in a surgical scenario.

The target subject refers to a site where the patient is to be operated on and/or an auxiliary device that plays a role in fixation. The site where the patient is to be operated on may include the head, hands, feet, etc. In some embodiments, the target subject may include the head of the patient on a surgical bed and/or a device worn on the head. The device worn on the head may be a device used for fixing the head of the patient. For example, during a surgical procedure, when the head of the patient on the surgical bed needs to be fixed, the target subject may include both the head of the patient on the surgical bed and the device worn on the head. As another example, during the surgical procedure, when the head of the patient on the surgical bed does not need to be fixed, the target subject may only include the head of the patient on the surgical bed. More descriptions regarding the target subject may be found in FIG. 1 and the related descriptions thereof.

The space where the target subject is located refers to the place where the target subject is located. For example, the space where the target subject is located may include an area in an operating room where the surgical bed is located, i.e., the space where the target subject is located may include the patient, the surgical bed, the medical personnel, the medical diagnostic auxiliary device, etc. The space where the target subject is located may include the target subject but is not limited to the target subject; it may include other objects in the space where the target subject is located.

In 320, a safety zone may be constructed for the target subject based on the first data. In some embodiments, operation 320 may be performed by the first construction module 220.

Figure 4A:
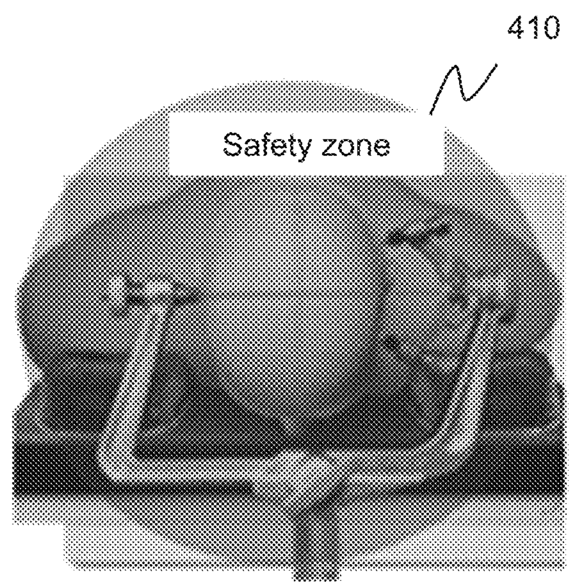
FIG. 4*a* is a schematic diagram illustrating an exemplary safety zone according to some embodiments of the present disclosure.

The safety zone refers to an area where the second acquisition device and the mechanical arm of the surgical robot are not allowed to enter during the process of collecting the second data. When the mechanical arm of the surgical robot moves outside the safety zone, it ensures that the target subject is not collided with, thus ensuring patient safety. In some embodiments, the safety zone may envelop the target subject in its internal space. For example, as shown in FIG. 4*a*, the safety zone 410 may be the enveloping sphere of the target subject. In some embodiments, the safety zone may be any other shape of spatial area enveloping the target subject, including but not limited to a cube, a cuboid, an ellipsoid, etc.

In some embodiments, when the mechanical arm carrying the second acquisition device collects the second data, it is not allowed to move into the safety zone. When it is determined through collision detection that the mechanical arm carrying the second acquisition device will interfere with the safety zone, the mechanical arm will stop moving, i.e., no objects within the safety zone will collide with the mechanical arm. In some embodiments, when the target subject includes the head of the patient and the device worn on the head, the mechanical arm will not collide with the head of the patient and the device worn on the head during autonomous motion. For example, during the subsequent collection of the second data to construct a three-dimensional model of the target subject, the mechanical arm will not collide with the head of the patient and the device worn on the head.

In some embodiments, the processor 190 may identify first subset data of the target subject based on the first data and construct the safety zone based on the first subset data.

The first subset data refers to data in the first data related to the target subject. For example, the first subset data may include a center position of the target subject, a radius of the target subject, or the like.

In some embodiments, the processor 190 may identify the first subset data in various ways. For example, the processor 190 may collect three-dimensional point cloud data of the target subject through the first acquisition device (e.g., a structured light depth camera) and segment the three-dimensional point cloud data of the target subject through point cloud segmentation. Then, the processor 190 may extract a facial feature of the target subject and fit the head to determine the first subset data of the target subject. As another example, the processor 190 may perform three-dimensional reconstruction through the first data collected by the first acquisition device (e.g., a binocular stereo camera), and then determine the first subset data of the target subject after the reconstruction. As yet another example, the first data may include depth image data and RGB image data. After matching the depth image data with the RGB image data, the processor 190 may perform image recognition on the RGB image data to identify the position of a target part in the RGB image data, and extract the first subset data of the target subject from the depth image data based on the position of the target part in the RGB image data. As still another example, the processor 190 may identify the first subset data through other manners. For example, the processor 190 may directly obtain discrete feature points through a target recognition algorithm and then identify the first subset data through a binocular stereo vision algorithm, which is not limited herein.

In some embodiments, the processor 190 may obtain maximum and minimum values of the target subject on x, y, and z axes from the first subset data, and then establish a cuboid based on the maximum and minimum values on the x, y, and z axes. Subsequently, the processor 190 may establish an enveloping sphere with a center of diagonal of the cuboid as a center of the enveloping sphere, and a length of the diagonal as a diameter of the enveloping sphere, and designate the enveloping sphere as the safety zone.

In some embodiments, the processor 190 may determine the first subset data of the target subject through the above manners, and extract the center position (e.g., the three-dimensional coordinates of the centroid or geometric center) of the target subject and/or the radius of the target subject. Then, based on the center position and a preset radius of the target subject, the processor 190 may determine a spherical region as the safety zone. The preset radius may be a radius set manually based on empirical values. For example, the preset radius may be 50 centimeters, 60 centimeters, etc. The preset radius may be an adaptively generated safety zone radius. For example, the preset radius may be obtained by multiplying the radius of the target subject by a safety factor (e.g., 2 times, 2.5 times, etc.), or by adding a safety threshold to the radius of the target subject (e.g., 20 centimeters, 25 centimeters, etc.).

In some embodiments, the adaptively generated safety zone radius may be related to a confidence level. For example, the processor 190 may respectively construct a three-dimensional model of the head of the patient based on the first data and head data collected before surgery (e.g., pre-operative head examination, etc.), match the two head three-dimensional models to determine a similarity between the two models, and designate the similarity as the confidence level. A lower confidence level indicates lower accuracy of the collected data, and in such cases, the safety zone radius may be increased to avoid collisions between the second acquisition device and the target subject during the collection of the second data. When the confidence level is lower than a preset confidence threshold, an auxiliary lighting device may be provided to increase the environment light, thereby improving the accuracy of the collected data. Then, the first data is re-collected, and a safety zone is constructed based on the new first data. In some embodiments, the processor 190 may also construct the safety zone in other manners. For example, the processor 190 may construct the safety zone by constructing a rectangular minimum bounding box, which is not limited herein.

By constructing the safety zone based on the first subset data in the first data collected by the first acquisition device to cause the second acquisition device to collect the second data outside the safety zone, the mechanical arm carrying the second acquisition device does not collide with the target subject during the collection of the second data, thereby ensuring the safety of the target subject.

In some embodiments, a size of the safety zone may be related to a count of historical actual acquisition points of a similar target subject. If a probability of overlap between the points composing a subject and the points composing the target subject exceeds a certain threshold after the subject undergoes a series of rigid motion transformations such as rotation, translation, etc., the subject is the similar target subject.

The count of historical actual acquisition points refers to a count of data acquisition points actually collected by the second acquisition device in historical data. For example, in the historical data, a total of 10 data acquisition points of the second acquisition device were set up, but after data of 6 data acquisition points were actually collected, a data coverage rate satisfies a requirement, then the count of the historical actual acquisition points is 6. More descriptions of the coverage rate may be found in FIG. 5 and the related descriptions thereof.

The larger the safety zone is, the more acquisition points are needed to make the coverage rate satisfy the requirement. Therefore, if there are too many historical actual acquisition points for the similar target subject, it means that the safety zone corresponding to the historical data might may be set too large.

There are too many historical actual acquisition points, which may lead to a long data collection time, a high processor load, etc. Therefore, when the count of historical actual acquisition points of the similar target subject exceeds a preset maximum threshold, the size of the safety zone may be appropriately reduced (e.g., by decreasing the radius of the safety zone), but it should not be smaller than the minimum safety zone threshold. The preset maximum threshold may be set based on experience, processor performance, or the like. For example, when the count of historical actual acquisition points exceeds 15, the collection time becomes lengthy, and the processor struggles with data processing, leading to potential errors, so the maximum point threshold may be set to 15. The minimum safety zone threshold may be set based on a size of a historically similar target subject. For example, the minimum safety zone threshold may be 5 cm larger than a radius of the target subject or 1.2 times the radius of the target subject to ensure patient safety during data collection. For example, if the radius of the target subject determined based on the first data is 12 cm, and the radius of the constructed safety zone is 24 cm, but when the safety zone for the similar target subject is set to 24 cm, the count of historical actual acquisition point counts is 20, which exceeds the preset maximum threshold of 15, then the radius of the safety zone may be set to 18 cm (e.g., the minimum safety threshold may be set to 17 cm).

In some embodiments of the present disclosure, the size of the safety zone is adjusted based on the count of historical actual acquisition points of the similar target subject, which allows for efficient and smooth collection of the second data while ensuring patient safety during second data collection.

In 330, second data outside the safety zone may be collected through a second acquisition device, wherein the second data is image data of the target subject. In some embodiments, operation 330 may be executed by the second acquisition module 230.

The second acquisition device refers to a device for collecting the second data. For example, the second acquisition device may include a structured light depth camera, a time-of-flight depth camera, a binocular stereo camera, etc. The second acquisition device is similar to the first acquisition device, which will not be repeated herein.

The second data refers to data that reflects the condition of the target subject, such as a position and shape characteristic, etc., of the target subject. In some embodiments, the second data may include a dataset of the target subject (e.g., three-dimensional spatial information of points on a surface of the target subject). In some embodiments, the second data may include depth image data, RGB image data, three-dimensional point cloud data, etc. For example, when the target subject is the head of the patient and the device worn on the head, the second data may be the depth image data and the RGB image data of the head of the patient and the device worn on the head. The second data may only include the dataset of the target subject, while the first data may include not only the dataset of the target subject but also the dataset of other objects in the space where the target subject is located.

In some embodiments, the processor 190 may determine a plurality of first acquisition points based on the safety zone and collect the second data sequentially at the plurality of first acquisition points using the second acquisition device. For example, the processor 190 may install the second acquisition device at an end of a mechanical arm. The mechanical arm may autonomously move around the target subject outside the safety zone to collect data around the target subject at the plurality of first acquisition points using the second acquisition device, thereby collecting image data of the target subject from different angles. As shown in FIG. **4*b*, a plurality of objects around the safety zone 410** represent second acquisition devices at the plurality of first acquisition points (i.e., a first acquisition point A, a first acquisition point B, a first acquisition point C, a first acquisition point D, a first acquisition point E, a first acquisition point F, a first acquisition point G, or a first acquisition point H).

Figure 5:
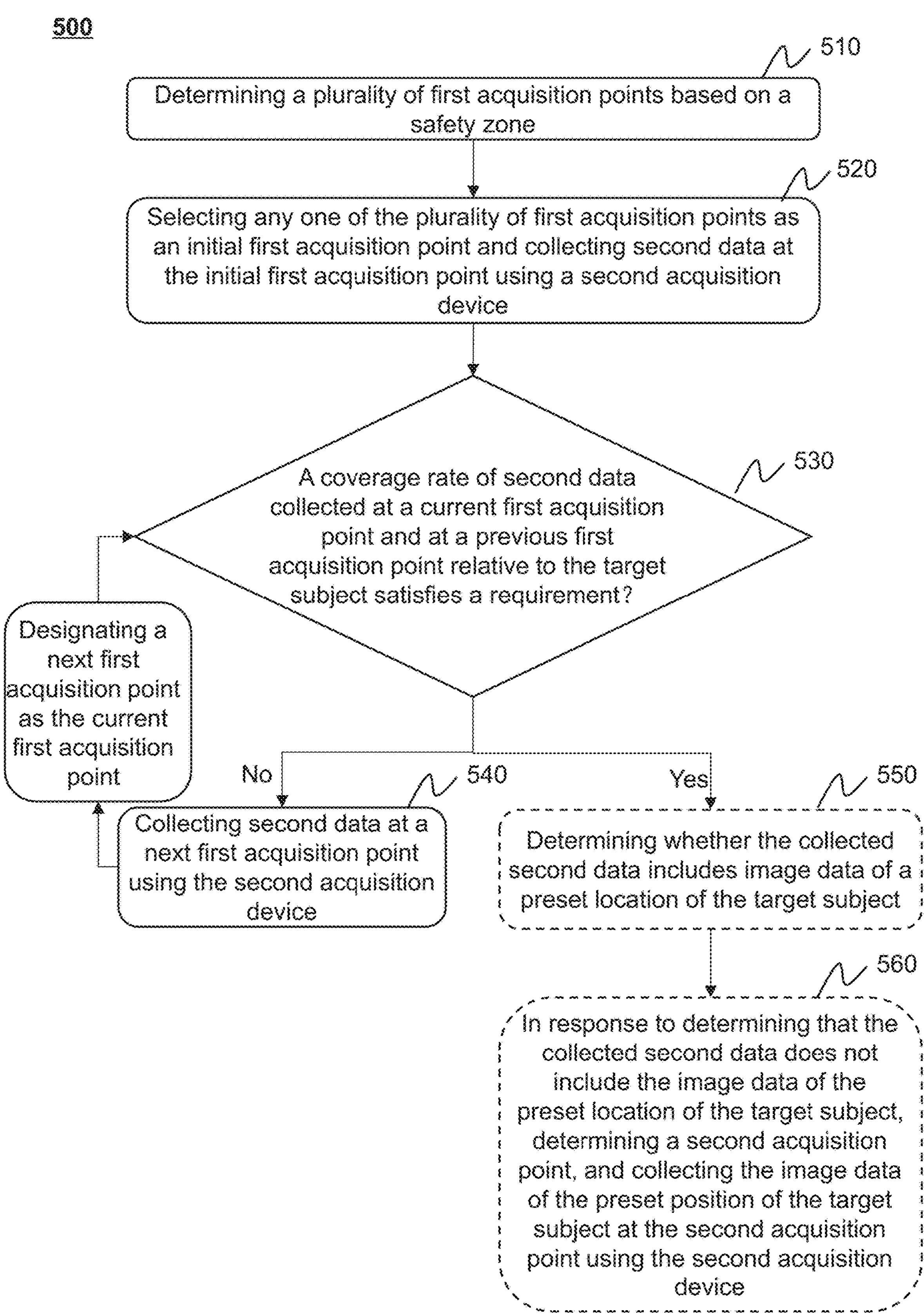
FIG. 5 is a flowchart illustrating an exemplary process for collecting second data according to some embodiments of the present disclosure.

More descriptions regarding collecting the second data outside the safety zone using the second acquisition device may be found in FIG. 5 and the related descriptions thereof.

In 340, a three-dimensional model of the target subject may be constructed based on the second data. The three-dimensional model of the target subject may be used for obstacle avoidance detection during the operation of the surgical robot. In some embodiments, operation 340 may be executed by the second construction module 240.

The three-dimensional model of the target subject refers to a model that reflects a geometric characteristic of the target subject in space. For example, when the target subject includes the head of the patient and the device worn on the head, the three-dimensional model of the target subject may include a three-dimensional model of the head of the patient and the device worn on the head.

In some embodiments, the processor 190 may construct the three-dimensional model of the target subject using techniques such as point cloud three-dimensional reconstruction, binocular vision reconstruction, etc. The processor 190 may also use other techniques to construct the three-dimensional model of the target subject, which is not limited herein.

Due to the safety zone constructed based on the first data collected by the first acquisition device being relatively large, for the target subject, if the surgical robot only performs the obstacle avoidance detection based on the safety zone during the surgical procedure, although the surgical robot can ensure avoiding the target subject, not entering the safety zone may result in the surgical robot being too far away from the target object, thereby making it impossible to reach a position closer to the target subject to assist medical personnel. Therefore, the processor 190 may achieve high-precision modeling of the target object based on the second data, allowing the surgical robot to perform the obstacle avoidance detection based on the high-precision three-dimensional model of the target object. In other words, the surgical robot may enter the safety zone without touching the target subject. Thus, the surgical robot can reach a position closer to the target object while ensuring patient safety, thereby providing higher levels of support and assistance to the medical personnel in the surgical procedure.

By collecting the first data through the first acquisition device and constructing the safety zone of the target subject based on the first data, and by collecting the second data outside the safety zone through the second acquisition device, the three-dimensional model of the target subject may be constructed, which allows the second acquisition device to collect the second data outside the safety zone, ensuring that the mechanical arm carrying the second acquisition device can avoid collisions with the target subject during data collection, thus ensuring the safety of the target subject. Moreover, the processor 190 can achieve high-precision modeling of the target subject based on the second data. Consequently, the surgical robot can reach a position closer to the target subject while ensuring patient safety, providing higher levels of support and assistance to the medical personnel during the surgical procedure.

In some embodiments, to achieve precise avoidance of the target subject while also avoiding other objects in the space where the target subject is located, and to address the issue of how to comprehensively perform obstacle avoidance with the surgical robot, the three-dimensional model of the target subject may be constructed based on the second data. Further, a three-dimensional model of the space where the target subject is located may be constructed based on the three-dimensional model of the target subject and an initial three-dimensional model, and the obstacle avoidance detection may be performed based on the three-dimensional model of the space.

In 350, an initial three-dimensional model of the space where the target subject is located may be constructed based on the first data. In some embodiments, operation 350 may be executed by the obstacle avoidance detection module 250.

The initial three-dimensional model refers to a three-dimensional model that reflects a space where the target subject is located, such as an area in an operating room where a surgical bed is located. In some embodiments, the initial three-dimensional model may include three-dimensional models of the patient, the medical personnel, the medical diagnostic auxiliary device, etc., in the surgical scenario. The initial three-dimensional model is a low-precision three-dimensional model corresponding to the space where the target subject is located.

In some embodiments, the processor 190 may construct the initial three-dimensional model of the space where the target subject is located based on the first data. In some embodiments, the processor 190 may determine a relative position of the target subject and the first acquisition device based on the first data, adjust a shooting angle of the first acquisition device based on the relative position, obtain new image data captured by the first acquisition device at the adjusted shooting angle, and designate the new image data as the first data for constructing the initial three-dimensional model.

Figure 7:
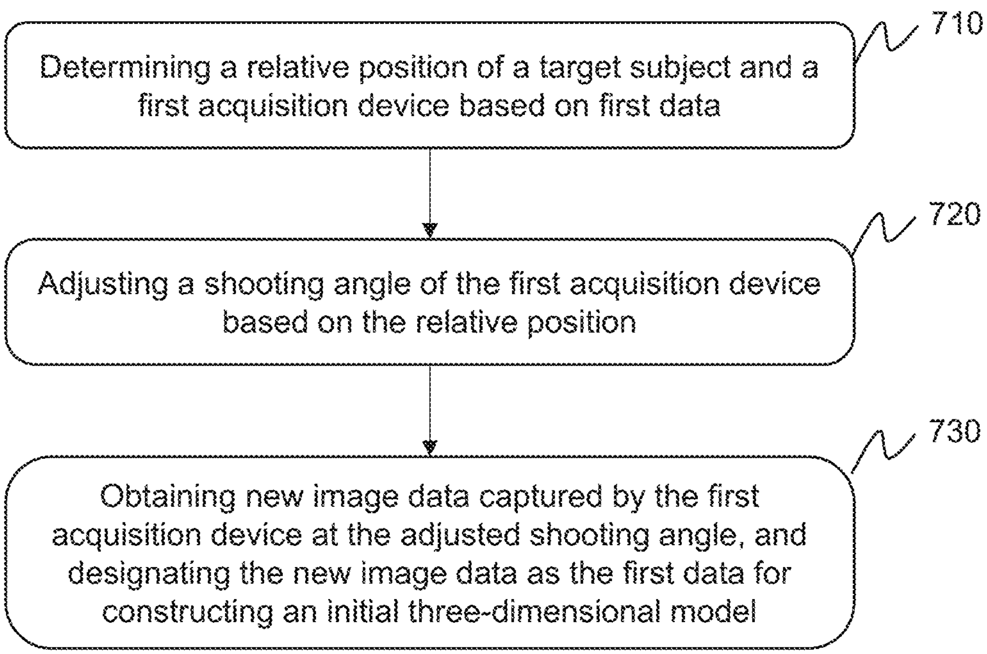
FIG. 7 is a flowchart illustrating an exemplary process for constructing an initial three-dimensional model of a space in which a target subject is located according to some embodiments of the present disclosure.

More descriptions regarding constructing the initial three-dimensional model of the space where the target subject is located based on the first data may be found in FIG. 7 and the related descriptions thereof.

In 360, the three-dimensional model of the space in which the target subject is located may be obtained based on the three-dimensional model of the target subject and the initial three-dimensional model of the space, and the obstacle avoidance detection may be performed based on the three-dimensional model of the space. In some embodiments, operation 360 may be executed by the obstacle avoidance detection module 250.

The three-dimensional model of the space where the target subject is located refers to a model including a high-precision target subject and low-precision other objects in the space where the target subject is located. For example, the three-dimensional model of the space may include the high-precision target subject and low-precision medical diagnostic auxiliary device, a surgical bed, and medical personnel. The high precision refers to a precision greater than or equal to a high-precision threshold, and the low precision refers to a precision lower than a low-precision threshold. The high-precision threshold and the low-precision threshold may be the same or different, and they may be determined based on experience.

In some embodiments, the processor 190 may combine the initial three-dimensional model and the three-dimensional model of the target subject to obtain the three-dimensional model of the space. For example, the processor 190 may perform point cloud stitching on the initial three-dimensional model and the three-dimensional model of the target subject to obtain the three-dimensional model of the space.

In some embodiments, the processor 190 may perform the obstacle avoidance detection based on the three-dimensional model of the space in various ways. For example, the processor 190 may perceive a position and a size of an object in the space based on the three-dimensional model of the space. When the mechanical arm of the surgical robot 130 moves, collisions with objects that the mechanical arm may encounter may be avoided during the movement process based on the pose of the mechanical arm.

During the operation process, the mechanical arm moves around the target subject most of the time. To ensure the safety of the target subject, it is particularly important to accurately avoid the target subject during the movement of the mechanical arm. Therefore, after the three-dimensional model of the target subject is obtained, it may be loaded into the initial three-dimensional model, and the safety zone of the target subject may be removed to obtain the three-dimensional model of the space. Then, collision detection may be performed by the mechanical arm in the three-dimensional model of the space for path planning.

In some embodiments, the first acquisition device may collect image data of the space where the target subject is located in real time and update the first data, and accordingly update the initial three-dimensional model of the space in real time, enabling the obstacle avoidance detection of a moving object in the space. For example, the position and movement of the medical personnel during surgery process are changing in real time, so this part of the content needs to be perceived online to achieve real-time collision avoidance. Real-time collection of the first data may be achieved by the first acquisition device, thereby obtaining real-time updated first data. By obtaining pose information of the moving object from the first data, the model corresponding to the moving object in the three-dimensional model of the space may be transformed accordingly based on the pose information, allowing real-time updates of the three-dimensional model of the space based on the change in the movement and position of the moving object. Thus, the three-dimensional model of the space can dynamically adapt to changes in the movement and position of the moving object in real-time. For example, if a medical personnel moves from position A to position B during the surgery process, the three-dimensional model corresponding to the medical personnel in the three-dimensional model of the space may adaptively move from position A to position B.

The first data collected in real-time by the first acquisition device allows for real-time perception of changes in the movement and position of the moving object in the actual space, thereby enabling adaptive adjustments and changes to the model corresponding to the moving object in the three-dimensional model of the space, thus enabling precise avoidance of dynamic obstacles by the surgical robot.

In some embodiments, the processor 190 may divide the three-dimensional model of the space into a plurality of regions, determine a simulation completeness degree for each region of the plurality of regions, and transmit the simulation completeness degree to the surgical robot for path planning.

The simulation completeness degree refers to a degree of completeness of the constructed three-dimensional model. For example, if a trash exists in a region but the trash is not included in the three-dimensional model constructed for the region, the simulation completeness degree of the region is relatively low.

In some embodiments, the processor 190 may divide the three-dimensional model of space into the plurality of regions based on importance levels. The importance level of a region may be determined based on a distance from the target subject to the region. The closer the region is to the target subject, the greater the impact on the surgery, and the higher the importance level of the region, thus a higher simulation completeness degree is required. For example, the processor 190 may set a spherical region with a radius of 50 cm centered on a center of the target subject as a first region; an annular spherical region with an inner radius of 50 cm and an outer radius of 100 cm centered on the center of the target subject as a second region; and an annular spherical region with an inner radius of 100 cm and an outer radius of 150 cm centered on the center of the target subject as a third region. In some embodiments, the processor 190 may divide the three-dimensional model of space into the plurality of regions based on an activity frequency of the surgical robot to distinguish the activity frequency of the surgical robot in different regions. The higher the activity frequency of the surgical robot, the higher the simulation completeness degree. For example, the processor 190 may divide the cuboid established based on the maximum and minimum values of the x, y, and z axes of the three-dimensional model of space into 27 regions, and determine the activity frequency of the surgical robot in the 27 regions based on historical data. For example, the processor 190 may set a region with an activity frequency in a range of 0 times/min-3 times/min as a first region, a region with an activity frequency in a range of 3 times/min-6 times/min as a second region, a region with an activity frequency in a range of 6 times/min-9 times/min as a third region, and a region with an activity frequency greater than 9 times/min as a fourth region.

In some embodiments, the processor 190 may determine the simulation completeness degree of each region of the plurality of regions through a simulation completeness determination model. More descriptions of determining the simulation completeness degree of each region of the plurality of regions may be found in FIG. 6 and the related descriptions thereof.

In some embodiments, the processor 190 may set the required simulation completeness degree for each region based on a condition of the region. For example, if the first region is closer to the target subject than the second region, and therefore, the importance level of the first region is higher than the importance level of the second region, the required simulation completeness degree for the first region may be set to 90% and the required simulation completeness degree for the second region may be set to 70%. As another example, if the activity frequency of the surgical robot is higher in the first region compared to the activity frequency of the surgical robot in the second region, indicating that the importance level of the first region is higher than the importance level of the second region, the required simulation completeness degree for the first region may be set to 80% and the required simulation completeness degree for the second region may be set to 60%.

In some embodiments, the processor 190 may adjust a collection process of the first acquisition device based on an actual simulation completeness degree of each region, thereby increasing the efficiency of the first acquisition device and reducing a likelihood of collisions. For example, if the required simulation completeness degree for the first region set by the processor 190 is 90%, but the actual simulation completeness degree of the first region is 85% (below 90%), the processor 190 may control the first acquisition device to increase the level of detail in collecting data for the first region during a next data collection process to improve the simulation completeness degree of the first region and reduce the likelihood of collisions. As another example, if the required simulation completeness degree for the second region set by the processor 190 is 60%, but the actual simulation completeness degree of the second region is 70% (above 60%), the processor 190 may control the first acquisition device to reduce the level of detail in collecting data for the second region during the next data collection process to improve efficiency.

By dividing the three-dimensional model of the space into the plurality of regions, determining the simulation completeness degree of each region of the plurality of regions, and adjusting the collection process of the first acquisition device accordingly, it is possible to increase the efficiency of the first acquisition device and reducing the likelihood of collisions. Additionally, a path may be planned more detailed and updated more timely for a region with a higher simulation completeness degree to achieve effective obstacle avoidance detection. For a region with a lower simulation completeness degree, appropriately reducing a frequency of path updates can save processor computing power and resources, ensuring smooth operation of obstacle avoidance detection.

In some embodiments of the present disclosure, constructing the safety zone based on the first data collected by the first acquisition device enables the second acquisition device to collect the second data outside the safety zone, which ensures that the mechanical arm carrying the second acquisition device can avoid collisions with the target subject while collecting the second data, thereby ensuring the safety of the target subject. Furthermore, by constructing the three-dimensional model of the target subject based on the second data and then constructing the three-dimensional model of the space based on the three-dimensional model of the target subject and the initial three-dimensional model, the obstacle avoidance detection can be performed based on the three-dimensional model of the space, thereby enabling precise avoidance of the target subject and avoiding other objects in the space where the target subject is located.

It should be noted that the description above regarding the obstacle avoidance process of the surgical robot is provided for illustration purposes only and does not limit the scope of the present disclosure. Those skilled in the art may make various modifications and changes to the obstacle avoidance process of the surgical robot under the guidance of the present disclosure. However, such modifications and changes remain within the scope of the present disclosure. In some embodiments, operations 350 to 360 may be omitted, and the surgical robot may perform obstacle avoidance based on the three-dimensional model of the target subject combined with techniques such as laser radar, ultrasonic sensors, and physical collision.

FIG. 5 is a flowchart illustrating an exemplary process for collecting second data according to some embodiments of the present disclosure. As shown in FIG. 5, process 500 includes the following operations. In some embodiments, one or more operations of process 500 shown in FIG. 5 may be implemented in the obstacle avoidance system 100 illustrated in FIG. 1. For example, process 500 shown in FIG. 5 may be stored in a storage device in the form of instructions that can be called and/or executed by the processor 190.

In 510, a plurality of first acquisition points may be determined based on a safety zone. In some embodiments, operation 510 may be performed by the second acquisition module 230.

A first acquisition point refers to a position where a second acquisition device collects second data. For example, the first acquisition point may be a position where the second acquisition device collects data of a target subject outside the safety zone. In some embodiments, the second acquisition device may collect image data of the target subject at the plurality of first acquisition points outside the safety zone, which may be used as the second data for constructing a three-dimensional model of the target subject.

In some embodiments, the processor 190 may divide a periphery of the safety zone into a plurality of regions in various ways. For example, the processor 190 may randomly divide the periphery of the safety zone into a plurality of regions with the same area. As another example, the processor 190 may divide the periphery of the spherical safety zone into eight uniform parts by using four circles with a vertical axis of the spherical safety zone as the diameter. As yet another example, the processor 190 may generate a new spherical region by using a center of the spherical safety zone as the center of the new spherical region, and use the radius of the spherical safety zone plus a preset radius value (e.g., 5 cm, 10 cm, 15 cm, 20 cm, etc.) as radius of the new spherical region, and then divide the periphery of the new spherical region into eight uniform parts using four circles with the vertical axis of the new spherical region as the diameter.

In some embodiments, the processor 190 may generate a first acquisition point around the periphery of each region of the plurality of regions based on a preset generation algorithm. A count of the preset generation algorithm may be more than one. For example, the processor 190 may randomly scatter eight points around the periphery of each region of the plurality of regions, and when two or more points appear around the periphery of the same region, the processor 190 may arbitrarily remove some points so that only one point is remained around the periphery of the region, which may be determined as the first acquisition point. As another example, the processor 190 may randomly set one point around the periphery of each region of the plurality of regions, then remove points that do not meet a requirement among the randomly set points around the periphery of the plurality of region, and the remaining points are determined as the first acquisition points. Points that do not meet the requirement may include point that a mechanical arm may not reach, a point where other parts of the mechanical arm may enter the safety zone when the second acquisition device is at the point, a point that interferes with the doctor, etc.

In some embodiments, an initial count of the plurality of first acquisition points may be determined based on a count of historical actual acquisition points. For example, if 15 first acquisition points were set for a similar target subject based on historical data, but a coverage rate satisfied a requirement after data was collected at only 10 first acquisition points, the count of first acquisition points may be appropriately reduced (e.g., reduced to 12, 13, or 14). More descriptions of the historical actual acquisition points may be found in FIG. 3 and the related descriptions thereof. More descriptions of the coverage rate may be found in operation 530 of FIG. 5 and the related descriptions thereof.

Determining the initial count of first acquisition points based on the count of historical acquisition points can avoid the arbitrariness of selecting the initial count of first acquisition points and reduce the count of first acquisition points while ensuring the coverage rate, thus improving acquisition efficiency.

In some embodiments, for any first acquisition point of the plurality of first acquisition points, the processor 190 may determine whether the coverage rate of second data collected at the first acquisition point and previous first acquisition points relative to the target subject satisfies a requirement. In response to determining that the coverage rate does not satisfy the requirement, the processor 190 may collect second data at a next first acquisition point using the second acquisition device; in response to determining that the coverage rate satisfies the requirement, the processor 190 may end the collection.

In some embodiments, the processor 190 may determine whether the collected second data includes image data of a preset location of the target subject. In response to determining that the collected second data does not include the image data of the preset location of the target subject, the processor 190 may determine a second acquisition point and collect the image data of the preset location of the target subject at the second acquisition point using the second acquisition device.

In some embodiments, the processor 190 may sequentially collect the second data at the plurality of first acquisition points using the second acquisition device by executing operations 520-560.

In 520, any one of the plurality of first acquisition points may be selected as an initial first acquisition point and the second data may be collected at the initial first acquisition point using the second acquisition device. In some embodiments, operation 520 may be performed by the second acquisition module 230.

Figure 4B:
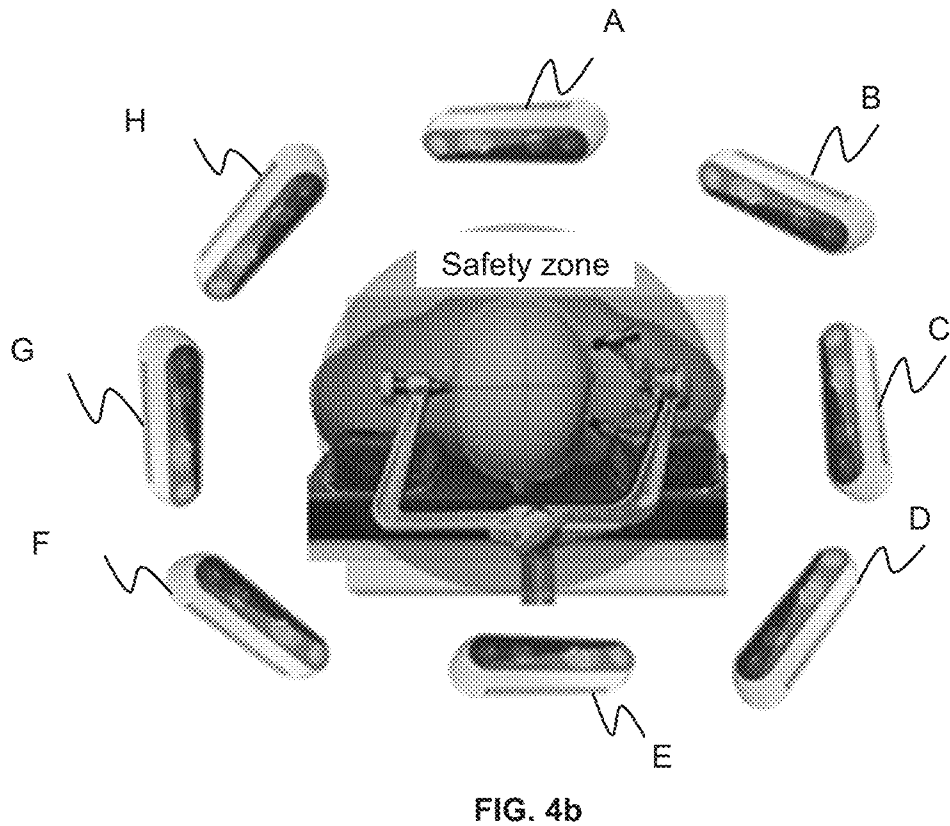
FIG. 4*b* is a schematic diagram illustrating an exemplary safety zone according to some embodiments of the present disclosure.

In some embodiments, as shown in FIG. 4*b*, the processor 190 may designate a first acquisition point A, a first acquisition point B, a first acquisition point C, a first acquisition point D, a first acquisition point E, a first acquisition point F, a first acquisition point G, and a first acquisition point H as the first acquisition points. The processor 190 may select any one of the plurality of first acquisition points (e.g., any one of the first acquisition point A, the first acquisition point B, the first acquisition point C, the first acquisition point D, the first acquisition point E, the first acquisition point F, the first acquisition point G, or the first acquisition point H) as the initial first acquisition point and collect second data based on the second acquisition device at the initial first acquisition point. The initial first acquisition point may be randomly selected.

In 530, whether the coverage rate of the second data collected at a current first acquisition point and previous first acquisition points relative to the target subject satisfies a requirement may be determined. In some embodiments, operation 530 may be executed by the second acquisition module 230.

The coverage rate refers to a ratio of an area of the safety zone covered by the collected second data to a total surface area of the safety zone. For example, if the area of the safety zone covered by the second data is 0.8 $m^2$ and the total surface area of the safety zone is 1 $m^2$, the coverage rate is 80%.

In some embodiments, the processor 190 may project the second data collected at the current first acquisition point and the previous first acquisition points onto a surface of the safety zone, determine a ratio of an area of the projection to the total surface area of the safety zone as the coverage rate. For example, when the second data is three-dimensional point cloud data of the target subject and the safety zone is an enveloping sphere, the three-dimensional point cloud data collected at the current first acquisition point and the previous first acquisition points may be projected onto the spherical surface of the safety zone, and the ratio of the projected area to the total surface area of the enveloping sphere may be determined as the coverage rate. In some embodiments, the coverage rate may be determined in other ways. For example, the processor 190 may determine the coverage rate by projecting the spherical projection onto the x, y, and z axes of the enveloping sphere. Manners of determining that coverage rate is not limited by the present disclosure.

In some embodiments, the processor 190 may compare the coverage rate of the data collected at the current first acquisition point and the previous first acquisition points with a preset minimum coverage rate threshold. If the coverage rate is greater than or equal to the minimum coverage rate threshold, the processor 190 may determine that the coverage rate satisfies the requirement; if the coverage rate is less than the minimum coverage rate threshold, the processor 190 may determine that the coverage rate does not satisfy the requirement. In some embodiments, the minimum coverage rate threshold may be determined based on the modeling accuracy. The higher the required modeling accuracy is, the higher the minimum coverage rate threshold may be. For example, the processor 190 may organize the minimum coverage rate threshold and the modeling accuracy into a data comparison table and determine the minimum coverage rate threshold based on the data comparison table. In some embodiments, the processor 190 may adjust the minimum coverage rate threshold based on a confidence level. When the confidence level is low, the minimum coverage rate threshold may be appropriately increased to avoid situations where the coverage rate is insufficient. More descriptions of the confidence level may be found in FIG. 3 and the related descriptions thereof.

In some embodiments, in response to determining that the coverage rate does not satisfy the requirement, the processor 190 may determine that the coverage rate of the second data collected at the current first acquisition point and the previous first acquisition points relative to the target subject is insufficient to reconstruct a high-precision three-dimensional model of the target subject. Then the processor 190 may proceed to operation 540 to collect data based on the second acquisition device at a next first acquisition point.

In 540, second data at a next first acquisition point may be collected using the second acquisition device. In some embodiments, operation 540 may be performed by the second acquisition module 230.

In some embodiments, in response to determining that the coverage rate does not satisfy the requirement, the processor 190 may sequentially collect data at the next first acquisition point based on the second acquisition device, designate the next first acquisition point as the current first acquisition point, and then repeat operations 530 to 560 to collect the second data. During the process of controlling the mechanical arm carrying the second acquisition device to move to the next first acquisition point, collision detection may be used to determine whether it will interfere with the safety zone, so as to adjust a movement path of the mechanical arm to the next first acquisition point to avoid collision with the target subject. If interference with the safety zone is detected during the movement of the mechanical arm, the mechanical arm may stop moving, or feedback may be provided to a user through an audio device, an indicator light, etc., to alert the user of a potentially hazardous operation and prompt the user to adjust the movement path accordingly.

In some embodiments, in response to determining that the coverage rate satisfies the requirement, the processor 190 may proceed to operations 550 to 560 to collect the second data including the preset location of the target subject.

By determining whether the coverage rate of the collected second data relative to the target subject satisfies the requirement, it ensures that modeling of the target subject based on the second data is achieved under a satisfactory condition and a high-precision three-dimensional model of the target object is obtained, which prevents low accuracy in reconstructing the three-dimensional model of the target subject due to insufficient coverage rate of the collected second data or issues such as redundant second data collection (i.e., continuing to collect data at the next first acquisition point even after the coverage rate satisfies the requirement), thereby enhancing modeling efficiency and accuracy.

In 550, whether the collected second data includes image data of a preset location of the target subject. In some embodiments, operation 550 may be executed by the second acquisition module 230.

The preset location of the target subject refers to a location used for registering a three-dimensional feature, a physiological characteristic, etc., of the target subject. For example, the preset location of the target subject may include the frontal face of the patient.

In some embodiments, the processor 190 may perform three-dimensional reconstruction based on the collected second data to obtain a three-dimensional model, conduct facial recognition on the three-dimensional model, and determine whether the collected second data includes image data of the preset location of the target subject based on the facial recognition result. In some embodiments, the processor 190 may process (e.g., statistical analysis, dot product, cross product, etc.) a vector representation of a surface formed by a plurality of adjacent points in the second data to determine a fluctuation degree of a surface of the target subject, and determine whether the collected second data includes data of the frontal face of the patient by comparing the fluctuation degree with standard facial data. The standard facial data may be obtained from historical data or preoperative scanning data of the patient. The comparison result may be expressed in terms of similarity. For example, if the similarity between the fluctuation degree of a certain part in the second data and the fluctuation degree of the standard facial data is greater than a preset similarity threshold (e.g., 80%, 85%, 90%, etc.), it may be determined that the collected second data includes the image data of the preset location of the target subject. Otherwise, it may be determined that the collected second data does not include the image data of the preset location of the target subject. In some embodiments, since the frontal face has more surface details and larger fluctuations compared to the side face and back of the head, the processor 190 may compare the fluctuation degree of the surface of the target subject with a preset fluctuation threshold. If a fluctuation degree greater than or equal to the preset fluctuation threshold exists, it may be determined that the second data includes the image data of the preset location of the target subject. Otherwise, it may be determined that the collected second data does not include the image data of the preset location of the target subject.

In some embodiments, in response to the determination that the collected second data does not include the image data of the preset location of the target subject, the processor 190 may proceed to operation 560 to collect second data including the preset location of the target subject.

In 560, a second acquisition point may be determined, and the image data of the preset position of the target subject may be collected at the second acquisition point using the second acquisition device. In some embodiments, operation 560 may be executed by the second acquisition module 230.

The second acquisition point refers to a location where the image data of the preset position of the target subject may be collected. For example, the second acquisition point may be a location where frontal face data of the patient may be collected.

In some embodiments, the processor 190 may determine a facial angle (e.g., the face in a side view, in an oblique view, etc.) in the existing second data based on a result of the three-dimensional reconstruction, thereby determining an orientation of the frontal face of the patient, and designating the location corresponding to the orientation of the frontal face of the patient as the second acquisition point. In some embodiments, a doctor may manually move the second acquisition device to the second acquisition point (e.g., the point location corresponding to the orientation of the frontal face of the patient). In some embodiments, the mechanical arm of the surgical robot may be controlled to move the second acquisition device to the second acquisition point to collect the image data of the preset location of the target subject.

In some embodiments, the processor 190 may designate the image data of the preset location of the target subject as the second data, thus obtaining the second data including the preset location of the target subject. By collecting the second data including the preset location of the target subject, facial registration can be achieved based on the second data, enabling accurate avoidance of the target subject during the movement of the mechanical arm.

In some embodiments, the processor 190 may not designate the image data of the preset location of the target subject as the second data. Instead, the processor 190 may perform the facial registration based on the image data collected at the second acquisition point, i.e., establishing a spatial transformation relationship between the three-dimensional model and an actual location, thereby mapping a surgical plan established based on the three-dimensional model to the actual location.

In some embodiments of the present disclosure, collecting the second data whose coverage rate satisfies the requirement, or the second data whose coverage rate satisfies the requirement and includes the image data of the preset location of the target subject, a high-precision three-dimensional model of the target subject can be obtained, enabling precise obstacle avoidance.

It should be noted that the description of the process of collecting the second data provided above is for illustrative purposes only, and does not limit the scope of the present disclosure. For those skilled in the art, various modifications and changes may be made to the process of collecting the second data under the guidance of the present disclosure, all of which are still within the scope of the present disclosure. In some embodiments, operations 550 to 560 may be omitted.

Figure 6:
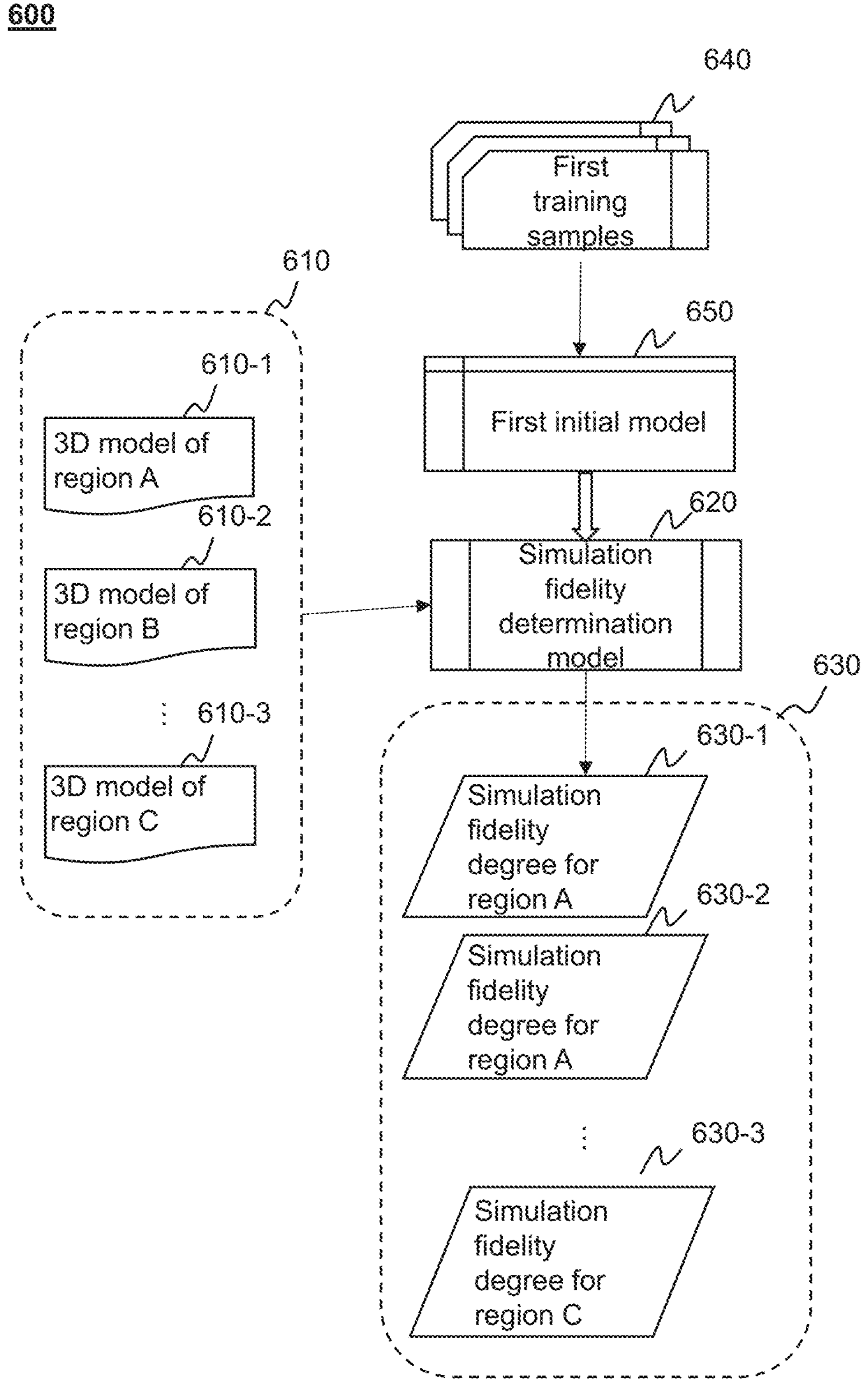
FIG. 6 is a flowchart illustrating an exemplary process for determining a simulation completeness degree for each region of a plurality of regions based on a simulation completeness determination model according to some embodiments of the present disclosure.

FIG. 6 is a flowchart illustrating an exemplary process for determining a simulation completeness degree for each region of a plurality of regions based on a simulation completeness determination model according to some embodiments of the present disclosure.

In some embodiments, a simulation completeness determination model 620 may be a deep learning neural network model. Exemplary deep learning neural network model may include a convolutional neural networks (CNN) model, a deep neural networks (DNN) model, a recurrent neural networks (RNN) model, or the like, or a combination thereof.

In some embodiments, as shown in FIG. 6, an input of the simulation completeness determination model 620 may include three-dimensional models 610 of the plurality of regions. The three-dimensional models 610 of the plurality of regions may include a three-dimensional model 610-1 of a region A, a three-dimensional model 610-2 of a region B, a three-dimensional model 610-3 of a region C, and so forth. More descriptions of the three-dimensional model of the space and the corresponding regions may be found in FIG. 3 and the related descriptions thereof. In some embodiments, an output of the simulation completeness determination model 620 may include a simulation completeness degree 630 for each region of the plurality of regions. The simulation completeness degree 630 for each region of the plurality of regions may include a simulation completeness degree 630-1 for the region A, a simulation completeness degree 630-2 for the region B, a simulation completeness degree 630-3 for the region C, and so forth.

In some embodiments, as shown in FIG. 6, a model parameter of the simulation completeness determination model 620 may be obtained by training a first initial model 650 using a plurality of first training samples 640. For example, the plurality of first training samples 640 may be obtained. Each of the plurality of first training samples 640 may include three-dimensional models of a plurality of regions of a sample space and a plurality of training labels. The plurality of regions of the three-dimensional models of the sample space may be the regions obtained by dividing the three-dimensional models of the sample space. The plurality of training labels may be the simulation completeness degrees of the plurality of regions of the three-dimensional models of the sample space. In some embodiments, the training labels may be obtained based on manual annotation.

A training process of the first initial model 650 may include one or more iterations. Merely by way of example, in a current iteration, for each of the plurality of first training samples 640, the processor 190 may determine the simulation completeness degrees of the plurality of regions of the sample space of the first training sample 640 based on a first intermediate model. If the current iteration is the first iteration, the first intermediate model may be the first initial model 650. If the current iteration is not the first iteration, the first intermediate model may be the model generated in a previous iteration. The processor 190 may determine a value of a loss function based on the accuracy of the simulation completeness degrees of the plurality of regions and update the first intermediate model based on the value of the loss function.

In some embodiments, the model parameter of the first initial model 650 may be iteratively updated based on the plurality of first training samples 640 so that the loss function of the first intermediate model satisfies a preset condition. For example, the preset condition may include the loss function converging, or the value of the loss function being less than a preset value. When the loss function satisfies the preset condition, the model training is completed, and the trained first initial model 650 may be determined as the simulation completeness determination model 620.

In some embodiments of the present specification, by determining the simulation completeness degrees of a plurality of regions based on the simulation completeness determination model, the simulation completeness degree of the plurality of regions can be obtained quickly and accurately, thereby improving the collection efficiency of the first acquisition device and reducing the possibility of collisions.

FIG. 7 is a flowchart illustrating an exemplary process for constructing an initial three-dimensional model of a space in which a target subject is located according to some embodiments of the present disclosure. As shown in FIG. 7, process 700 includes the following operations. In some embodiments, one or more operations of process 700 shown in FIG. 7 may be implemented in the obstacle avoidance system 100 shown in FIG. 1. For example, process 700 shown in FIG. 7 may be stored in the form of instructions in a storage device that can be called and/or executed by the processor 190.

In 710, a relative position of the target subject and a first acquisition device may be determined based on first data. In some embodiments, operation 710 may be performed by the obstacle avoidance detection module 250.

The relative position refers to a directional relationship between a position of the target subject and a position of the first acquisition device. In some embodiments, the relative position may be a directional relationship between a vertical axis of the target subject and a central axis of the first acquisition device. For example, the relative position may include a frontal position and a bilateral position. The frontal position refers to that the vertical axis of the target subject is in the same direction as the central axis of the first acquisition device; the bilateral position refers to that the vertical axis of the target subject is perpendicular to the central axis of the first acquisition device.

In some embodiments, the processor 190 may perform feature recognition on the target subject based on the first data to obtain a pose of the target subject. Then, the processor 190 may determine the relative position of the target subject and the first acquisition device based on positional information in the pose of the target subject and positional information of the first acquisition device.

In some embodiments, medical personnel may directly determine the pose and position of the target subject, thereby determining the relative position of the target subject and the first acquisition device, and then inputting the relative position into a user terminal, which is transmitted to the processor 190 via a network.

In 720, a shooting angle of the first acquisition device may be adjusted based on the relative position. In some embodiments, operation 720 may be performed by the obstacle avoidance detection module 250.

The shooting angle of the first acquisition device refers to an angle between the central axis of the first acquisition device and a static reference line in the space where the target subject is located. The static reference line refers to a line that remains stationary in the space where the target subject is located. For example, the shooting angle of the first acquisition device may be the angle between the central axis of the first acquisition device and a central axis of a surgical cart.

In some embodiments, the processor 190 may automatically determine an adjusted angle based on the relative position using a preset algorithm. In some embodiments, medical personnel may adjust the shooting angle of the first acquisition device based on the adjusted angle of the first acquisition device. In some embodiments, the processor 190 may automatically adjust the shooting angle of the first acquisition device based on the adjusted angle of the first acquisition device.

In some embodiments, the processor 190 may adjust the shooting angle of the first acquisition device based on the position of the target subject in the space or based on an operating position. For example, the operation performed on the target subject may include a surgical procedure. During the surgical procedure, the first acquisition device captures an image of the space where the target subject is located to obtain the first data, and then three-dimensional reconstruction is performed based on the first data to obtain an initial three-dimensional model. To reconstruct the initial three-dimensional model that highly matches the real scenario and to better achieve active obstacle avoidance, the first acquisition device needs to have a good shooting angle, capturing spatial image data covering the space where the target subject is located. Therefore, the shooting angle of the first acquisition device may be adjusted by adjusting the adjusted angle. The adjusted angle is an angle the first acquisition device needs to adjust to.

For example, in a surgical scenario with a patient as a center, both a medical diagnostic auxiliary device and medical personnel are positioned around the patient. Thus, a central position of the patient in the surgical scenario may be identified from the first data, and the shooting angle of the first acquisition device may be adjusted so that the central position lies on a midline (e.g. dashed lines in FIGS. 8*a* and 8*b*) of a range of the shooting angle of the first acquisition device. At this point, the first acquisition device has a relatively good shooting angle and may capture more comprehensive first data.

As another example, the medical personnel may pre-set a current operating position, such as the frontal position or the bilateral position. Different operating positions may correspond to different pre-set shooting angles, which may be experimentally determined to provide a highest coverage rate. Therefore, by determining the corresponding shooting angle based on the current operating position, the first acquisition device may be adjusted to the shooting angle for spatial image capture, thereby obtaining the first data with the highest coverage rate for subsequently reconstruction of the initial three-dimensional model consistent with the real scenario.

Figure 8A:
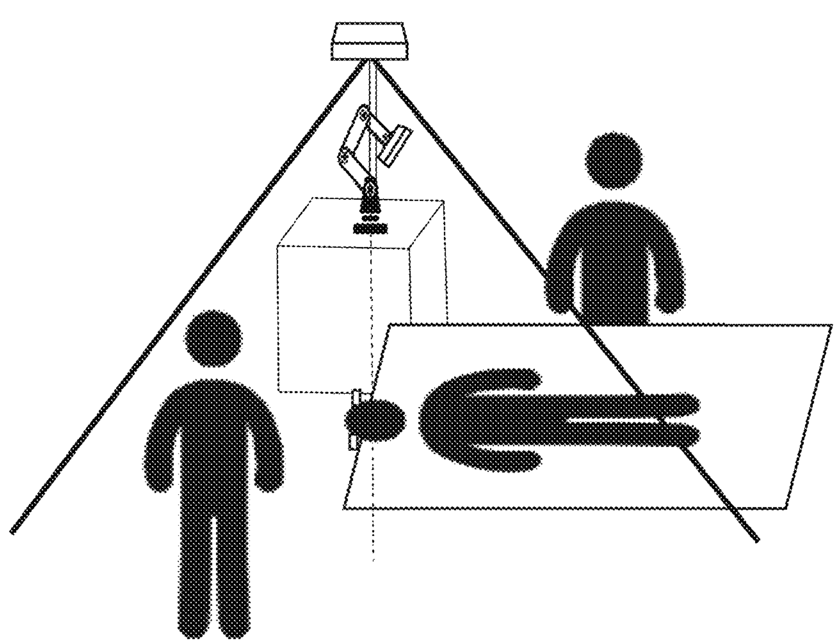
FIG. 8*a* is a schematic diagram illustrating adjusting a shooting angle of a first acquisition device according to some embodiments of the present disclosure.
Figure 8B:
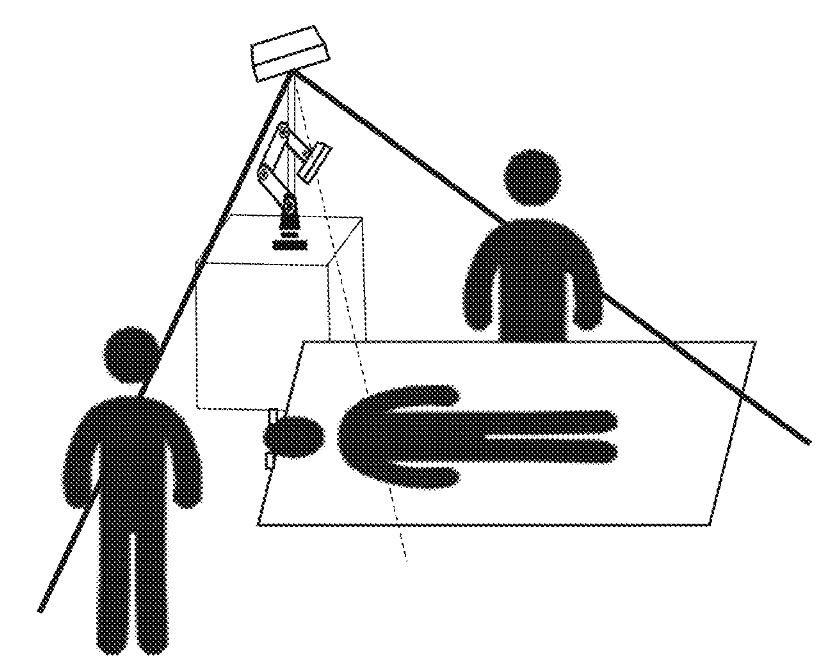
FIG. 8*b* is a schematic diagram illustrating adjusting a shooting angle of a first acquisition device according to some embodiments of the present disclosure.

Taking FIGS. 8*a* and 8*b* as an example, in which the operating position is the bilateral position. In FIG. 8*a*, the shooting angle of the first acquisition device is not adjusted. At this time, a field of view of the first acquisition device is the region between the shooting angle lines (represented by the thick black lines in FIGS. 8*a* and 8*b*), where it's evident that the medical personnel on the right-side are not within the field of view. Consequently, the initial three-dimensional model established based on the first data at this time does not include the model of the medical personnel on the right-side, thus a mechanical arm may not actively avoid the medical personnel on the right-side during autonomous movement.

In FIG. 8*b*, the shooting angle of the first acquisition device has been adjusted. At this time, the field of view of the first imaging device is the region between the shooting angle lines, and all medical personnel are within the shooting angle. The initial three-dimensional model established based on the first data at this time may include models of all medical personnel, enabling the mechanical arm to actively avoid all medical personnel during autonomous movement.

In some embodiments, the processor 190 may automatically determine an adjusted shooting angle based on the relative position using a preset algorithm, thereby determining the adjusted angle.

In some embodiments, the processor 190 may determine, through a correction value determination model, a correction value of the adjusted angle based on the type of surgery, participant information, and the adjusted angle. More descriptions of determining the correction value of the adjusted angle through the correction value determination model may be found in FIG. 9 and the related descriptions thereof.

In 730, new image data captured by the first acquisition device at the adjusted shooting angle may be obtained and the new image data may be designated as the first data for constructing the initial three-dimensional model. In some embodiments, operation 730 may be performed by the obstacle avoidance detection module 250.

The new image data refers to image data captured by the first acquisition device at the adjusted shooting angle.

In some embodiments, the processor 190 may designate the new image data as the first data and construct the initial three-dimensional model of the space where the target subject is located based on the first data. More descriptions of constructing the initial three-dimensional model of the space where the target subject is located based on the first data may be found in FIG. 3 and the related descriptions thereof.

In some embodiments of the present disclosure, by adjusting the shooting angle of the first acquisition device to capture the first data in a better field of view, a comprehensive initial three-dimensional model simulating the real scenario can be obtained, thereby improving obstacle avoidance accuracy.

It should be noted that the above description of the process for constructing the initial three-dimensional model of the space where the target subject is located is for illustration and explanation purposes only, and does not limit the scope of the present disclosure. For those skilled in the art, various modifications and changes may be made to the process for constructing the initial three-dimensional model of the space where the target subject is located under the guidance of the present disclosure.

Figure 9:
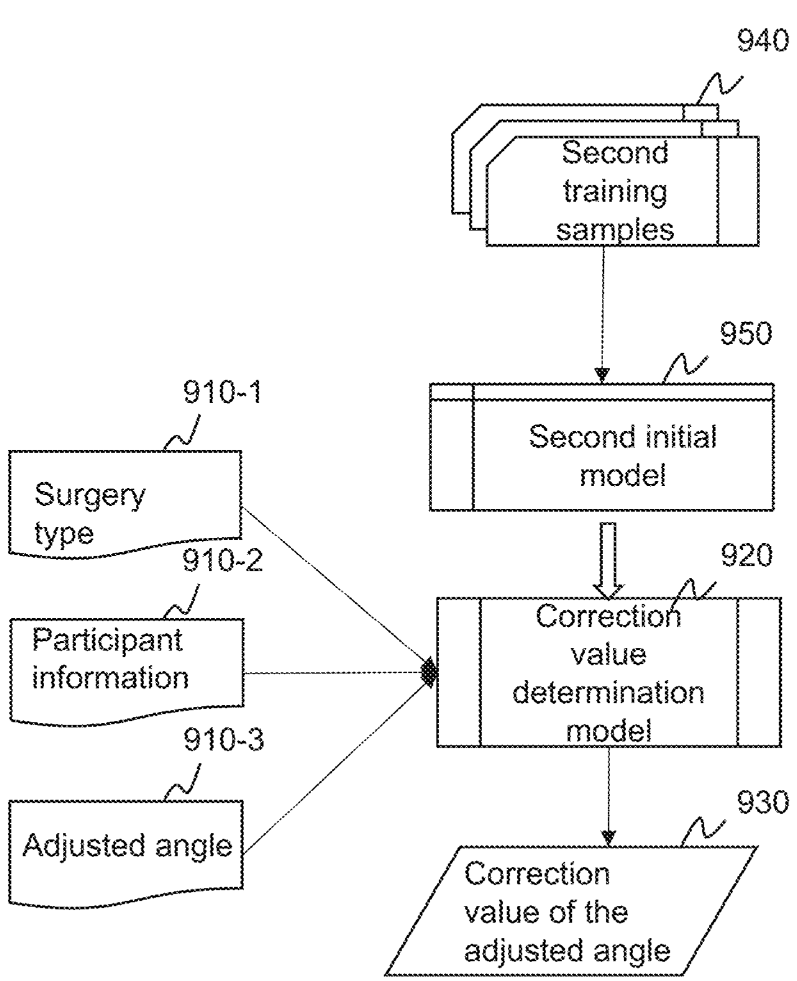
FIG. 9 is a schematic diagram illustrating determining a correction value of an adjusted angle based on a correction value determination model according to some embodiments of the present disclosure.

FIG. 9 is a schematic diagram illustrating determining a correction value of an adjusted angle based on a correction value determination model according to some embodiments of the present disclosure.

In some embodiments, a correction value determination model 920 may be a deep learning neural network model. Exemplary deep learning neural network model may include a convolutional neural networks (CNN) model, a deep neural networks (DNN) model, a recurrent neural networks (RNN) model, or the like, or a combination thereof.

In some embodiments, as shown in FIG. 9, an input of the correction value determination model 920 may include a surgery type 910-1, participant information 910-2, and an adjusted angle 910-3. In some embodiments, an output of the correction value determination model 920 may include the correction value 930 of the adjusted angle.

The surgery type 910-1 may include cranial trauma surgery, craniotomy surgery, minimally invasive head surgery, etc. Different types of surgeries have different requirements for the operating position of medical personnel and the positioning of medical auxiliary devices. Therefore, the surgery type 910-1 may affect the adjusted angle. In some embodiments, the surgery type 910-1 may be represented as a vector. For example, the surgery type 910-1 may be represented as [a], where 'a' represents the surgery type.

The participant information 910-2 may include a count and a level of participants. The participants may include medical personnel. Since the count and the level of the participants may affect the operating position of the participants during surgery, the participant information 910-2 may affect the adjusted angle. For example, if a surgical scenario includes 5 participants and the first data captured by the first acquisition device includes 3 participants, after the adjusted angle is automatically determined through the preset algorithm, the correction value determination model may evaluate whether adjusting the shooting angle based on the automatically determined adjusted angle will cover more participants, thus determining the correction value of the adjusted angle, and accordingly making the adjustment more effective. In some embodiments, the participant information 910-2 may be represented as a vector. For example, the participant information 910-2 may be represented as [b, c], where 'b' represents the count of the participants and 'c' represents the level of the participants.

In some embodiments, as shown in FIG. 9, the correction value determination model 920 may be obtained by training a second initial model 950 based on a plurality of second training samples 940. For example, a plurality of second training samples 940 may be obtained. Each of the plurality of second training samples 940 may include a sample surgery type, sample participant information, a sample adjusted angle, and a training label. The training label may be a correction value of the sample adjusted angle. In some embodiments, the training label may be obtained based on manual annotation.

A training process of the second initial model 950 may include one or more iterations. For example, in a current iteration, the processor 190 may use a second intermediate model to determine the correction value of the adjusted angle of each of the plurality of second training samples 940. If the current iteration is the first iteration, the second intermediate model may be the second initial model 950. If the current iteration is not the first iteration, the second intermediate model may be the model generated in a previous iteration. The processor 190 may determine a value of a loss function based on the accuracy of the correction value of the adjusted angle of the plurality of second training samples 940, and update the second intermediate model based on the value of the loss function.

In some embodiments, a model parameter of the second initial model 950 may be iteratively updated based on the plurality of second training samples 940, so that the loss function of the second intermediate model satisfies a preset condition. For example, the preset condition may include the loss function converging, the value of the loss function being less than a preset value, etc. When the loss function satisfies the preset condition, the model training is completed, and the trained second initial model 950 may be determined as the correction value determination model 920.

In some embodiments of the present disclosure, by determining the correction value of the adjusted angle through the correction value determination model, it is possible to quickly and accurately obtain the correction value of the adjusted angle, thereby obtaining a more accurate adjusted angle and achieving a more comprehensive coverage rate for an intraoperative scenario.

Figure 10:
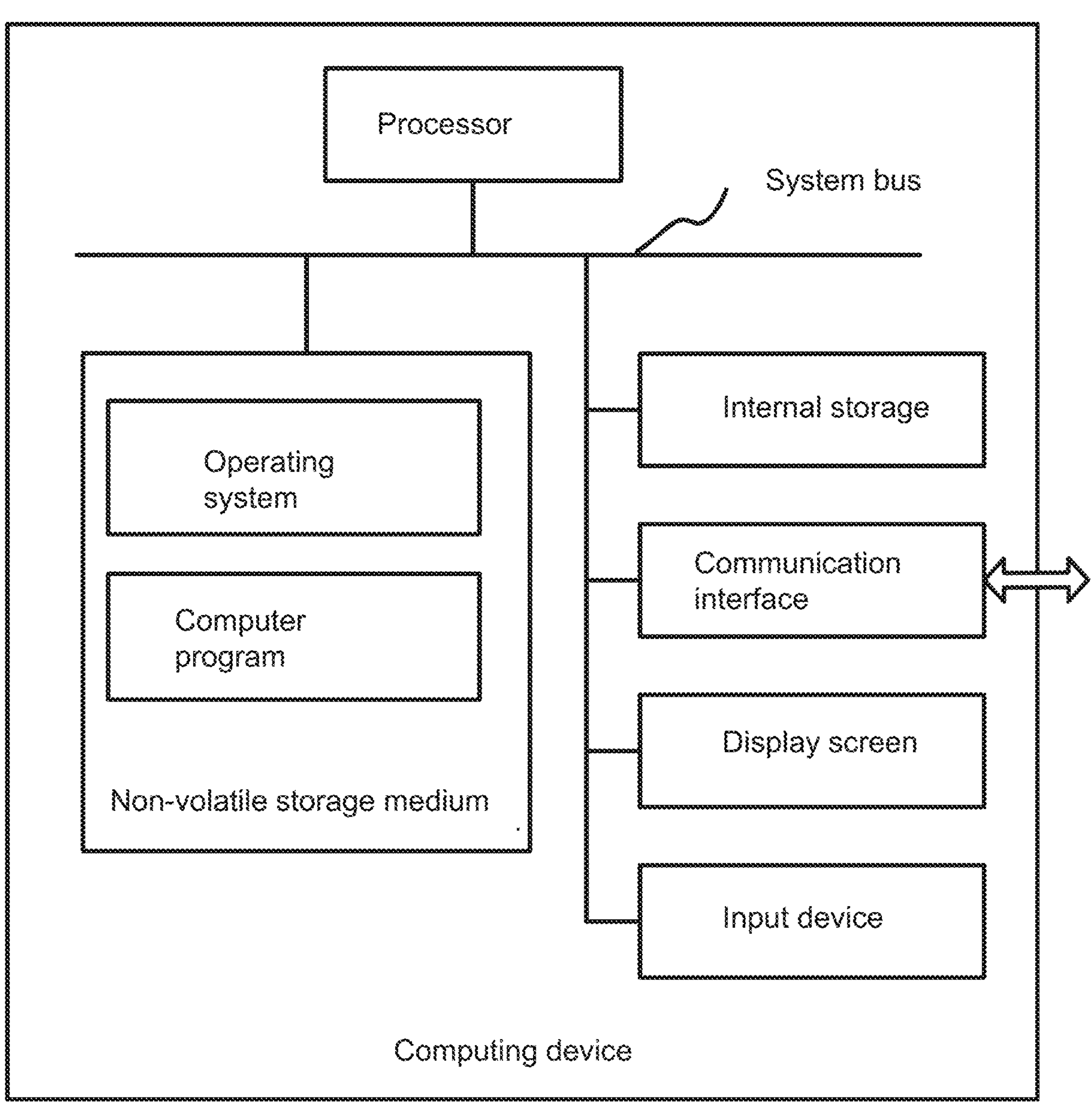
FIG. 10 is a schematic diagram illustrating an internal structure of a computing device according to some embodiments of the present disclosure.

FIG. 10 is a schematic diagram illustrating an internal structure of a computing device according to some embodiments of the present disclosure.

The computing device may include a processor, a storage, a communication interface, a display screen, and an input device that are connected via a system bus. The processor of the computing device may provide computing and control capabilities. The storage of the computing device may include a non-volatile storage medium and an internal storage. The non-volatile storage medium may store an operating system and computer programs. The internal storage may provide an environment for the operation of the operating system and the computer programs in the non-volatile storage medium. The communication interface of the computing device may be configured to communicate with an external terminal via a wired manner or a wireless manner, where the wireless manner may be implemented through WiFi, a carrier network, near field communication (NFC), or the like. When executed by the processor, the computer programs realize a method for model construction. The display screen of the computing device may be an LCD screen, an e-ink display, or the like, and the input device of the computing device may be a touch layer overlaid on the display screen, a button, a trackball, a touchpad, etc., set on an outer casing of the computing device, or an external keyboard, a touchpad, a mouse, etc.

Those skilled in the art may understand that the structure shown in FIG. 10 is only a schematic diagram of the relevant part of the structure associated with the present disclosure, and does not constitute a limitation on the computing device to which the present disclosure is applied. Specific computing devices may include more or fewer components than shown in the drawing, or may combine certain components, or may have different arrangements of components.

One embodiment of the present disclosure provides a computing device comprising a storage and a processor, wherein the storage stores computer programs, and the processor, when executing the computer programs, implements the operations of the methods described in the above embodiments.

One embodiment of the present disclosure provides a computer-readable storage medium storing computer instructions. When reading the computer programs from the storage medium, a computer implements the operations of the methods described in the above embodiments.

Those skilled in the art may understand that all or part of the processes in the embodiments described above may be implemented by instructing relevant hardware through the computer programs. The computer programs may be stored in a non-volatile computer-readable storage medium. When executed, the computer programs may include the processes of the embodiments described above. The references to storage, memory, databases, or other media used in various embodiments provided herein may include at least one of a non-volatile storage and a volatile storage. The non-volatile storage may include a read-only storage (ROM), a magnetic tape, a floppy disk, a flash storage, an optical storage, or the like. The volatile storage may include a random access storage (RAM), an external cache storage, or the like. As an illustration and not limitation, RAM may take various forms, such as a static random access storage (SRAM), a dynamic random access storage (DRAM), or the like.

In some embodiments, the device for obstacle avoidance of the surgical robot may include a processor and a storage, wherein the storage may be configured to store an instruction set, and the processor may be configured to execute the instruction set to implement the method for obstacle avoidance of the surgical robot.

In some embodiments, the computer-readable storage medium may store computer instructions. When reading the computer instructions from the storage medium, a computer implements the method for obstacle avoidance of the surgical robot.

The beneficial effects that may result from the embodiments of the present disclosure may include but are not limited to: (1) By constructing the safety zone based on the first data collected by the first acquisition device, the second acquisition device can collect the second data outside the safety zone, which ensures that the mechanical arm carrying the second acquisition device can avoid collision with the target subject when collecting the second data, thereby ensuring the safety of the target subject. Furthermore, by constructing the three-dimensional model of the target subject based on the second data, constructing the three-dimensional model of the space where the target subject is located based on the three-dimensional model of the target subject and the initial three-dimensional model, and performing obstacle avoidance detection based on the three-dimensional model of the space, precise avoidance of the target subject can be achieved while also avoiding obstacles in the space where the target subject is located. (2) By collecting the second data whose coverage rate satisfies the requirement and includes the preset location of the target subject, a high-precision three-dimensional model of the target subject can be obtained, thereby achieving precise obstacle avoidance. (3) By determining the simulation completeness degree of each region of a plurality of regions through the simulation completeness determination model, the simulation completeness degree of each region of the plurality of regions can be quickly and accurately obtained, thereby increasing the collection efficiency of the first acquisition device and reducing the likelihood of collisions. (4) By adjusting the shooting angle of the first acquisition device, the first acquisition device can collect first data under a better field of view, obtaining an initial three-dimensional model that comprehensively simulates the real scenario, thereby improving obstacle avoidance accuracy. (5) By determining the correction value of the adjusted angle through the correction value determination model, the correction value of the adjusted angle can be obtained quickly and accurately, thereby obtaining a more accurate adjusted angle and ensuring more comprehensive coverage rate of the intraoperative scenario.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure; For example, the terms "one embodiment," "an embodiment," and/or "some embodiments" mean that a particular feature, structure, or characteristic described in connection with the embodiment is included in at least one embodiment of the present disclosure; Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure;

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

As another example, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameter set forth in the written description and attached claims are approximations that may vary depending upon the desired properties sought to be obtained by a particular embodiment. In some embodiments, the numerical parameter should be construed in light of the number of reported significant digits and by applying ordinary rounding techniques. Notwithstanding that the numerical ranges and parameter setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrating of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for obstacle avoidance of a surgical robot implemented by a system including a first acquisition device, a second acquisition device, a processor, and the surgical robot, the method comprising:

causing the first acquisition device to collect first data, wherein the first data is image data of a space in which a target subject is located;

causing the processor to construct a safety zone for the target subject based on the first data;

causing the second acquisition device to collect second data outside the safety zone, wherein the second data is image data of the target subject, the second acquisition device is carried by a mechanical arm of the surgical robot to collect the second data, and the second acquisition device and the mechanical arm are not allowed to move into the safety zone during the process of collecting the second data; and causing the processor to construct a three-dimensional model of the target subject based on the second data; and causing the processor to perform obstacle avoidance detection based on the three-dimensional model of the target subject during an operation of the surgical robot.

2. The method of claim 1, wherein the causing the processor to construct a safety zone for the target subject based on the first data includes:

causing the processor to identify first subset data of the target subject based on the first data;

causing the processor to determine a center position of the target subject based on the first subset data; and causing the processor to determine a spherical region as the safety zone based on the center position and a preset radius.

3. The method of claim 1, wherein the causing the second acquisition device to collect second data outside the safety zone includes:

causing the processor to determine a plurality of first acquisition points based on the safety zone, the plurality of first acquisition points being positions outside the safety zone where the second acquisition device collects the second data; and causing the second acquisition device to sequentially collect the second data at the plurality of first acquisition points.

4. The method of claim 3, wherein the causing the processor to determine a plurality of first acquisition points based on the safety zone includes:

causing the processor to divide the safety zone into a plurality of regions; and causing the processor to generate the plurality of first acquisition points around a periphery of the plurality of regions based on a preset generation algorithm.

5. The method of claim 3, wherein the causing the second acquisition device to sequentially collect the second data at the plurality of first acquisition points includes:

for any first acquisition point of the plurality of first acquisition points, causing the processor to determine whether a coverage rate of second data collected at the first acquisition point and previous first acquisition points relative to the target subject satisfies a requirement;

in response to determining that the coverage rate does not satisfy the requirement, causing the second acquisition device to collect second data at a next first acquisition point; and in response to determining that the coverage rate satisfies the requirement, causing the processor to end the collection.

6. The method of claim 5, wherein the coverage rate is a ratio of an area of the safety zone covered by the second data collected at the first acquisition point and the previous first acquisition points to a total surface area of the safety zone, and the requirement includes that the coverage rate is greater than a preset minimum coverage rate threshold.

7. The method of claim 3, further comprising:

causing the processor to determine whether the collected second data includes image data of a preset location of the target subject;

in response to determining that the collected second data does not include the image data of the preset location of the target subject, causing the processor to determine a second acquisition point, and causing the second acquisition device to collect the image data of the preset position of the target subject at the second acquisition point.

8. The method of claim 1, wherein the second acquisition device is located at an end of the mechanical arm of the surgical robot.

9. The method of claim 1, further comprising:

causing the processor to construct an initial three-dimensional model of the space in which the target subject is located based on the first data;

causing the processor to determine a three-dimensional model of the space in which the target subject is located based on the three-dimensional model of the target subject and the initial three-dimensional model of the space, and causing the processor to perform the obstacle avoidance detection based on the three-dimensional model of the space.

10. The method of claim 9, wherein the causing the processor to construct an initial three-dimensional model of the space in which the target subject is located based on the first data includes:

causing the first acquisition device to update the first data in real time; and causing the processor to construct the initial three-dimensional model of the space in which the target subject is located based on the updated first data.

11. The method of claim 9, wherein the method further includes:

causing the processor to divide the three-dimensional model of the space into a plurality of regions;

causing the processor to determine a simulation completeness degree of three-dimensional models constructed for each region of the plurality of regions;

causing the processor to determine a required simulation completeness degree for each region based on a distance of the region to the target subject and an activity frequency of the surgical robot in the region; and causing the first acquisition device to adjust a collection process of the first acquisition device based on the simulation completeness degree and the required simulation completeness degree of each region.

12. The method of claim 9, wherein the causing the processor to construct an initial three-dimensional model of the space in which the target subject is located based on the first data includes:

causing the processor to determine a relative position of the target subject and the first acquisition device based on the first data;

causing the first acquisition device to adjust a shooting angle of the first acquisition device based on the relative position;

causing the first acquisition device to obtain new image data at the adjusted shooting angle; and causing the first acquisition device to designate the new image data as the first data for constructing the initial three-dimensional model.

13. The method of claim 12, wherein the causing the first acquisition device to adjust a shooting angle of the first acquisition device based on the relative position includes:

causing the processor to determine an adjusted angle based on the relative position;

causing the processor to determine, through a correction value determination model, a correction value of the adjusted angle based on a type of surgery, participant information, and the adjusted angle, the correction value determination model being a deep learning neural network model; and causing the first acquisition device to adjust the shooting angle of the first acquisition device based on the correction value of the adjusted angle.

14. The method of claim 1, wherein the first acquisition device and the second acquisition device are integrated into a same device.

15. The method of claim 14, wherein one of the first acquisition device and the second acquisition device is canceled, and functions of the first acquisition device and the second acquisition device are implemented by the other of the first acquisition device and the second acquisition device.

16. The method of claim 2, wherein the preset radius is an adaptively generated safety zone radius determined by the processor by:

constructing three-dimensional models of a head of the target subject based on the first data and head data collected before surgery;

determining a similarity of the three-dimensional models of the head as a confidence level of the first data; and determining the preset radius based on the confidence level, the preset radius being negatively correlated with the confidence level.

17. The method of claim 1, wherein a size of the safety zone is determined by the processor based on a count of historical actual acquisition points of a similar target subject of the target subject, the count of historical actual acquisition points is a count of data acquisition points collected by the second acquisition device in historical data when a data coverage rate corresponding to the similar target subject satisfies a requirement.

18. The method of claim 9, wherein:

the causing the processor to determine a three-dimensional model of the space includes:

causing the processor to load the three-dimensional model of the target subject into the initial three-dimensional model of the space; and causing the processor to determine the three-dimensional model of the space by removing the safety zone of the target subject from the initial three-dimensional model loaded with the three-dimensional model of the target subject, the causing the processor to perform the obstacle avoidance detection based on the three-dimensional model of the space includes: the causing the processor to perform path planning for the mechanical arm of the surgical robot in the three-dimensional model of the space.

19. A system for obstacle avoidance of a surgical robot, comprising a first acquisition device, a second acquisition device, the surgical robot, and a processor, wherein the first acquisition device is configured to collect first data, wherein the first data is image data of a space in which a target subject is located;

the second acquisition device is configured to collect second data outside a safety zone of the target subject, wherein the second data is image data of the target subject, the second acquisition device is carried by a mechanical arm of the surgical robot to collect the second data, and the second acquisition device and the mechanical arm are not allowed to move into the safety zone during the process of collecting the second data;

the surgical robot is configured to perform a surgical procedure;

the processor is configured to:

construct the safety zone based on the first data; and construct a three-dimensional model of the target subject based on the second data; and perform obstacle avoidance detection based on the three-dimensional model of the target subject during an operation of the surgical robot.

20. A computer-readable storage medium storing computer instructions, wherein when reading the computer instructions from the storage medium, a computer implements the method for obstacle avoidance of a surgical robot, wherein the method comprises:

causing a first acquisition device to collect first data, wherein the first data is image data of a space in which a target subject is located;

causing the computer to construct a safety zone for the target subject based on the first data;

causing a second acquisition device to collect second data outside the safety zone, wherein the second data is image data of the target subject, the second acquisition device is carried by a mechanical arm of the surgical robot to collect the second data, and the second acquisition device and the mechanical arm are not allowed to move into the safety zone during the process of collecting the second data; and causing the computer to construct a three-dimensional model of the target subject based on the second data; and causing the computer to construct an initial three-dimensional model of the space in which the target subject is located based on the first data;

causing the computer to determine a three-dimensional model of the space in which the target subject is located based on the three-dimensional model of the target subject and the initial three-dimensional model of the space, and causing the computer to perform obstacle avoidance detection based on the three-dimensional model of the space during an operation of the surgical robot.

* * * * *